United States Patent [19]

Mach

[11] Patent Number: 5,994,082
[45] Date of Patent: Nov. 30, 1999

[54] METHODS FOR THE IDENTIFICATION OF INHIBITORS WHICH SUPPRESS THE ACTIVITY OF PROTEINS DISPLAYING CIITA ACTIVITY

[76] Inventor: Bernard Mach, 45 Route de Pregny, 1292 Chambèsy, Geneva, Switzerland

[21] Appl. No.: 08/519,547

[22] Filed: Aug. 25, 1995

[30] Foreign Application Priority Data

Aug. 26, 1994 [EP] European Pat. Off. .............. 94113378

[51] Int. Cl.⁶ .................................................... G01N 33/53
[52] U.S. Cl. ............................................ 435/7.1; 530/350
[58] Field of Search .................................. 435/172.3, 7.1; 530/350

[56] References Cited

U.S. PATENT DOCUMENTS 5,672,473 9/1997 Glimcher et al. ............................ 435/6

OTHER PUBLICATIONS

Mach, B. et al., MHC Class II–Deficient Combined Immunodeficiency: a Disease of Gene Regulation, *Immunol. Rev*., 138, pp. 207–221 (1994).

Mach, B. et al., MHC Class I and Class II, *Res. Immunol*., 144, pp. 525–526 (1993).

Reith, W. et al., Cloning of RF—X, the MHC Class II Promoter Binding Protein Affected in a Hereditary Defect in Class II Gene Regulation, Experientia, 45, pp. a22 abstract 73 (1989).

Steimle, V. et al., Cloning of an HLA Class II Transactivator Defective in a Form of Primary Immunodeficiency by Genetic Complementation, Experientia, pp. a7 abstract 41 (1993).

Glimcher, et al. 1992. Ann. Rev. Immunol. vol. 10, pp. 13–49. "Sequences and Factors: A guide to MHC Class II Transcription".

Steimle, et al. 1993. Cell. vol. 75 pp. 135–146. "Complementation Cloning of an MHC Class II Transactivator Mutated in Hereditiry . . .".

*Primary Examiner*—Nancy Degen
*Assistant Examiner*—Irem Yucel
*Attorney, Agent, or Firm*—Fish & Neave; James F. Haley, Jr.; Scott D. Miller

[57] ABSTRACT

The invention relates to inhibitors suppressing the activity of transacting proteins which are essential for the general control of vertebrate MHC class II gene expression and methods for identifying the same. The invention additionally relates to pharmaceutical compositions containing said inhibitors, preferably for the treatment of diseases which are associated with an aberrant expression of MHC class II genes.

4 Claims, 15 Drawing Sheets

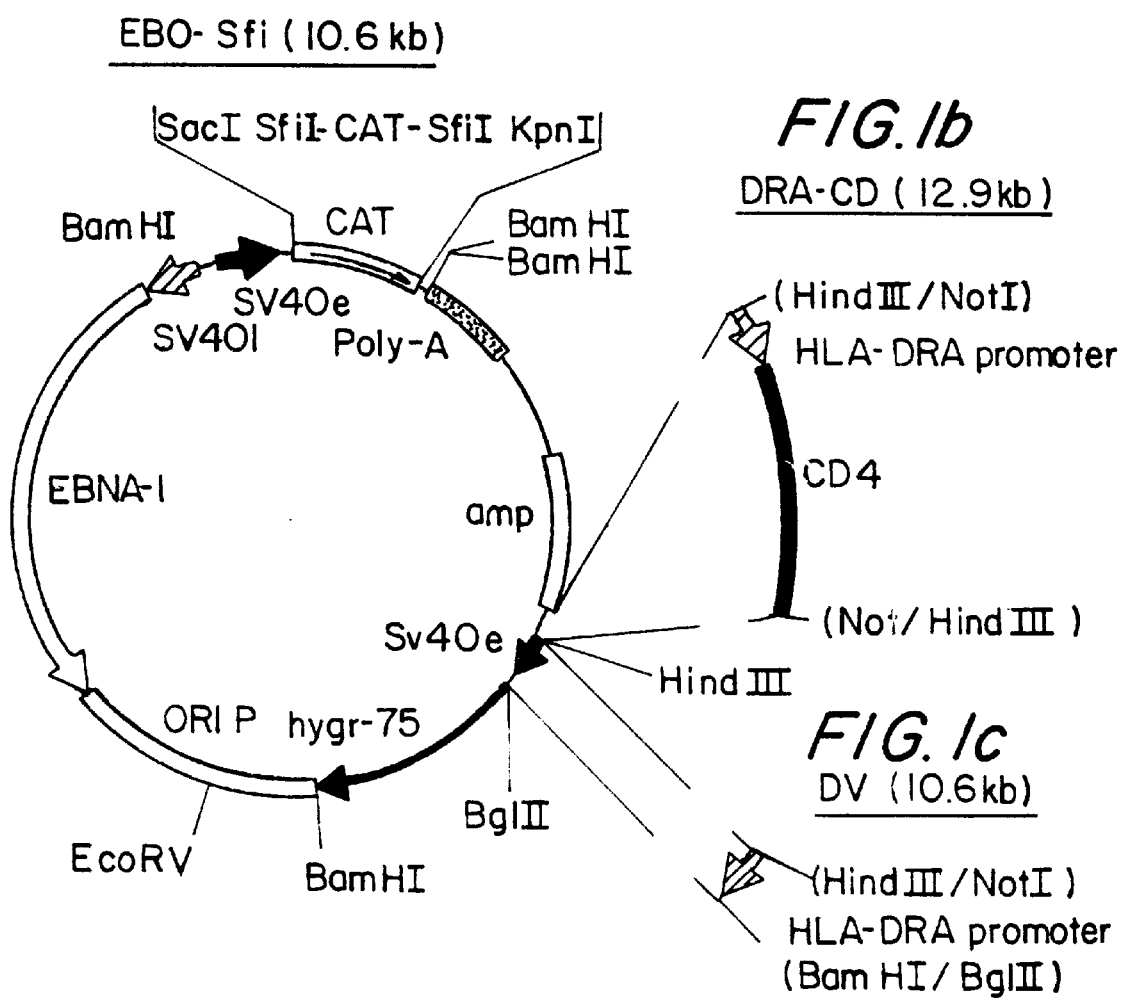

FIG. 3a

```

#GATGAGGCTGTGTGTCCTTCTGAGCTGGACATCCTTGGGAAGCTGAGGGCACGAGAGGGCTGCCAGACTCCGGGAGCT                                              90
   *
GCTGCCTGGCTGGGATTCCTACACAATGCGTTGCCTGGCCTCCAAGGCCCCAAGGCAGCTCACAGTGC                                                         180
                        M  R  C  L  A  P  R  P  Q  G  S  S  Q  C                                                              22

TGCCACCATGGAGTTGGGGCCCCTAGAAGGTGGCTACCTGGAGCTTCTTAACAGTGATGCTGACCCCCTGTGCCTTTACCACTTCTATGA                                   270
 A  T  M  E  L  G  P  L  E  G  G  Y  L  E  L  L  N  S  D  A  D  P  L  C  L  Y  H  F  Y  D                                     52

CCAGATGGACCTGGCTGGAGAAGAAGATTGAGCTCTACTCAGAACCGACACAGACACCATCAACTGCGACCAGTTCAGCAGGCTGTT                                      360
 Q  M  D  L  A  G  E  E  E  I  E  L  Y  S  E  P  D  T  D  T  I  N  C  D  Q  F  S  R  L  L                                    82
                                              acidic GTGTGACATGGAAGGTGATGAAGAGACCAGGGAGGCTTATGCCAATATCGCGGAACTGGACCAGTATGTCTTCCAGGACTCCCAGCTGGA                                   450
 C  D  M  E  G  D  E  E  T  R  E  A  Y  A  N  I  A  E  L  D  Q  Y  V  F  Q  D  S  Q  L  E                                   112

GGGCCTGAGCAAGGACATTTTCAAGGACATATAGGACCAGATGAAGTGATCGGTGAGAGTATGGAGATGCCAGCAGAAGTGGGCAGAAAAG                                  540
 G  L  S  K  D  I  F  K  H  H  I  G  P  D  E  V  I  G  E  S  M  E  M  P  A  E  V  G  Q  K  S                                142

TCAGAAAAGACCCTTCCCAGAGGAGCTTCCGGCAGAGCTGAAGCACTGGAAGCCAGCTGAGCCCCACTGTGGTGACTGGCAGTCTCCT                                     630
 Q  K  R  P  F  P  E  E  L  P  A  D  L  K  H  W  K  P  A  E  P  P  T  V  V  T  G  S  L  L                                   172

AGTGGGACCAGTGAGCGACTGCTCCACCCTGCCCTGCCACTGCCTGCCTGTTCAACCAGGAGCCAGCTCCGGCCAGATGCGCCT                                         720
 V  G  P  V  S  D  C  S  T  L  P  C  L  P  L  P  A  L  F  N  Q  E  P  A  S  G  Q  M  R  L                                   202
                   I                                                      II

GGAGAAAACCGACCAGATTCCCATGCCTTTCTCCAGTTCCTCCGTTGAGCTGCCTGAATCTCCCTGAGGACCATCCAGTTTGTCCCAC                                    810
 E  K  T  D  Q  I  P  M  P  F  S  S  S  L  S  C  L  N  L  P  E  G  P  I  Q  F  V  P  T                                      232

CATCTCCACTCTGCCCCATGGGCTCTGGCAAATCTCTGAGGCTGAACAGGGTCTCCAGTATATTCATCTACCATGGTGAGGTGCCCA                                     900
 I  S  T  L  P  H  G  L  W  Q  I  S  E  A  G  T  G  V  S  S  I  F  I  Y  H  G  E  V  P  Q                                   262
                                                                                  III

GGCCAGCCAAGTACCCCTCCCAGTGGATTCACTGTCCCAACATCTCCAGACCGGCCAGGCTCCACCAGCCCCTTCGCTCC                                             990
 A  S  Q  V  P  P  S  G  F  T  V  I  I  G  L  P  T  S  P  D  R  P  G  S  T  S  P  F  F  A  P                                292
```

FIG. 3b

```
ATCAGCCACTGACCTGCCCAGCATGCCTGAACCTCCCGAGCAAACATGACAGAGCACAAGAGCACAAGAGTCCCCACCCAATGCCC  1080
 S  I  S  H  *  T  C  P  A  M  P  E  P  A  L  T  S  R  A  N  M  T  E  H  K  T  S  P  T  Q  C  P   322
      S  A  T  D  L  P  S  M  P  E  P  A  L  T  S  R  A  N  M  T  E  H  K  T  S  P  T  Q  C  P

GGCAGCTGGAGAGTCTCCAACAAGCTTCCAAAATGCCTGAGCCGTGGAGCCAGTTCTACCGCTCACTGCAGGACACGTATGGTGCCGA  1170
  A  A  G  E  V  S  N  K  L  P  K  W  P  E  P  V  E  Q  F  Y  R  S  L  Q  D  T  Y  G  A  E   352

GCCCGCAGGCCCGGATGGCATCCTAGTGGAGGTGGATCTGGTGCAGGCCAGGCTGGAGAGGAGCAGCAGCAAGAGCCTGGAGCGGGAACT  1260
  P  A  G  P  D  G  I  L  V  E  V  D  L  V  Q  A  R  L  E  R  S  S  S  K  S  L  E  R  E  L   382

GGCCACCCCGGACTGGGCAGAACGGCAGCTGGCCCAAGGAGGCCTGGCTGAGGTGCTGTTGGCTGCTGCAGGAGCACCGGCGGCCGGTGA  1350
  A  T  P  D  W  A  E  R  Q  L  A  Q  G  G  L  A  E  V  L  L  A  A  K  E  H  R  R  P  R  E   412

GACACGAGTGATTGCTGTGCTGGGCAAAGCTGGTCAGGGCAAAGAGCCTGGGGCAGTGAGCCGGGCCTGGGCTTGTGGCCGGCT  1440
  T  R  V  I  A  V  L  G  K  A  G  Q  G  K  S  Y  W  A  G  A  V  S  R  A  W  A  C  G  R  L   442

TCCCCAGTACGACTTTGTCTTCTGTCCCCTGCCATTGCTTGAACCGTCTGCAGGATCGTCTGCTCCCT  1530
  P  Q  Y  D  F  V  F  S  V  P  C  H  C  L  N  R  P  G  D  A  Y  G  L  Q  D  L  L  F  S  L   472

GGGCCCACAGCCACTCGTGGCGGCCGATGAGGTTTTCAGCCACATCTTGAAGAGACCTGACCGCGTTCTGCTCATCCTAGACGCCTTCGA  1620
  G  P  Q  Q  P  L  V  A  A  D  E  V  F  S  H  I  L  K  R  P  D  R  V  L  L  I  L  D  A  F  E   502

GGAGCTGGAAGCGCAAGATGGCTTCCTGCACAGCACGTGCGGAGCCCTGCTCCCTCCCGGGGCTGCTGGCCGGCCT  1710
  E  L  E  A  Q  D  G  F  L  H  S  T  C  G  P  A  P  A  E  P  C  S  L  R  G  L  L  A  G  L   532

TTTCCAGAAGAAGCTGCTCCGAGGTTGCACCCTTGCACCCTCCCTCCTCCTCACAGCCCGGCGCCCTGGTCCAGAGCCTGAGCAGGCCGACGC  1800
  F  Q  K  K  L  L  R  G  C  T  L  L  T  A  R  P  R  G  R  L  V  Q  S  L  S  K  A  D  A   592

CCTATTTGAGCTGTCCGGCTTCTCCATGGAGCAGGCCCAGGCCATACGTGATGGCTACTTTGAGAGTCAGGGATGACAGAGCACCAAGA  1890
  L  F  E  L  S  G  F  S  M  E  Q  A  Q  A  Y  V  M  R  Y  F  E  S  S  G  M  T  E  H  Q  D   622

CAGAGCCCTGACGTGTCCGGACCCCACTCTTCTCAGTCACAGCCCACTTTGTGCCGGCAGTGTGCCAGCTCTCAGA  1980
  R  A  L  T  L  L  R  D  R  P  L  L  L  S  H  S  H  S  P  T  L  C  R  A  V  C  Q  L  S  E   652
```

FIG. 3c

```
GGCCCTGCTGGAGCTTGGGGAGGACGCCAAGCTGCCCTCCACGCTCACGGGACTCTATGTCGGCCTGCTGGGCCGTGCAGCCCTGACAG    2070
 A  L  E  L  G  E  D  A  K  L  P  S  T  L  T  G  L  Y  V  G  L  L  G  R  A  A  L  D  S       652

CCCCCCGGGGCCCTGGCAGAGCTGGCCAAGCTGGCCTGGGAGCTGGCCAAGCTACCCTACAGGAGGACCAGTTCCCATC               2160
 P  P  G  A  L  A  E  L  A  K  L  A  W  E  L  G  R  R  H  Q  S  T  L  Q  E  D  Q  F  P  S    682

CGCAGACGTGAGGACCTGGGCATGGCCAAAGGCTTAGTCCAACACCCGCGGGCCGCAGAGTCCGAGCTGGCCTTCCCCAGCTTCCT        2250
 A  D  V  R  T  W  A  M  A  K  G  L  V  Q  H  P  P  R  A  A  E  S  E  L  A  F  P  S  F  L    712

CCTGCAATGCTTCCTGGGGCCCTGTGGCTGGCTCTGAGTGGCGAAATCAAGGACAAGGAGCTCCCGCAGTACCTAGCATTGACCCCAAG    2340
 L  Q  C  F  L  G  A  L  W  L  A  L  S  G  E  I  K  D  K  E  L  P  Q  Y  L  A  L  T  P  R    742

GAAGAAGAGGCCCTATGACAACTGGCTGGAGGGCGTGCCACGCTTTCTGGCTGGGCTGATCTTCCAGCCTCCCGCCCGTGCCTGGGAGC    2430
 K  K  R  P  Y  D  N  W  L  E  G  V  P  R  F  L  A  G  L  I  F  Q  P  P  A  R  C  L  G  A    772

CCTACTCGGGCCATCGGCCGCTGCCTCGGTGGACAGGAAGCAGAGGTCGAGCTACCTGAAGCGGCTGCAGCCGGGGACACTGCG         2520
 L  L  G  P  S  A  A  A  S  V  D  R  K  Q  K  V  L  A  R  Y  L  K  R  L  Q  P  G  T  L  R    802

GGCGCGGCAGCTGCTTGAGCTGCTGCACTGCGCCCACGAGGCCGAGGAGGCCGAGGCCGAATTGGCAGCAGCTGGTGTACAGGAGCTCCCCGGCCG    2610
 A  R  Q  L  L  E  L  L  H  C  A  H  E  A  E  E  A  G  I  W  Q  H  V  V  Q  E  L  P  G  R    832

CCTCTCTTTTCTGGGCACCCGCCTCACGCCCCTCCTGATGCACATGTACTGGGACCTTGGAGGCGGCCAAGACTTCTCCCTGGA         2700
 L  S  F  L  G  T  R  L  T  P  P  D  A  H  V  L  G  K  A  L  E  A  A  G  Q  D  F  S  L  D    862

CCTCCGCAGCACTGGCATTGCCCCTCCGGGCAGCCTGGGAGACCTCAGTGGTGTCACCCGTTTCAGGGCTGCCTTGAGCGACAC          2790
 L  R  S  T  G  I  C  P  S  G  L  G  S  L  V  G  L  S  C  V  T  R  F  R  A  A  L  S  D  T    892

GGTGGGCGCTGTGGAGAGTCTGCGGCAGCATGGGGAGACAAAGCTACTTCAGGCAGCAGGAGAAGTTCACCATCGAGCCTTTCAAAGC     2880
 V  A  L  W  E  S  L  R  Q  H  G  E  T  K  L  L  Q  A  A  E  E  K  F  T  I  E  P  F  K  A    922

CAAGTCCCTGAAGGATGTGGAAGACCTGGGCAAAGCTTGTGCAGACTCAGAGGACGAGAAGTTCCTCGGAAGACACAGTGGGGAGCTCCC    2970
 K  S  L  K  D  V  E  D  L  G  K  L  V  Q  T  Q  R  T  R  S  S  E  D  T  A  G  E  L  P       952
```

FIG. 3d

```
TGCTGTTCGGGACCTAAAGAAACTGGAGTTTGCGCTGGGCCCTGTCTCAGGCCCCCAGGCTTTCCCCAAACTGGTGCGGATCCTCACGGC    3060
 A  V  R  D  L  K  K  L  E  F  A  L  G  P  V  S  G  P  Q  A  F  P  K  L  V  R  I  L  T  A     982

CTTTTCCTCCCTGACCATCTGGACCTGGATGCGCTGAGTGAGAACAAGATCGGGGACGAGGGTGTCTCGCAGCTCTCAGCCACCTTCCC    3150
 F  S  S  L  Q  H  L  D  L  D  A  L  S  E  N  K  I  G  D  E  G  V  S  Q  L  S  A  T  F  P    1012

CCAGCTGAAGTCCTTGGAAACCCTCAATCTGTCCCAGAACAACATCACTGACCTGGGTGCCTACAAACTCGCCGAGGCCCTGCCTTCGCT    3240
 Q  L  K  S  L  E  T  L  N  L  S  Q  N  N  I  T  D  L  G  A  Y  K  L  A  E  A  L  P  S  L    1042

CGCTGCATCCCTGCTCAGGCTAAGCTTGTACAATAACTGCATCTGCGACGTGGAGCCGAGAGCTTGGCTCGTGTGCTTCCGGACATGGT    3330
 A  A  S  L  L  R  L  S  L  Y  N  N  C  I  C  D  V  G  A  E  S  L  A  R  V  L  P  D  M  V    1072

GTCCCTCCGGGTGATGGACGTCCAGTACAACAAGTTCACGGCTGCCGGGCCCAGCAGCTCGCTGCCAGCCTTCGGAGGTGTCCTCATGT    3420
 S  L  R  V  M  D  V  Q  Y  N  K  F  T  A  A  G  A  Q  Q  L  A  A  S  L  R  R  C  P  H  V    1102

GGAGACGCTGGCGATGTGGACGCCACCATCAGTGTCCAGGAACACCTGCAACAACAGAGATTCAGGGATCAGCCTGAGATGATC         3510
 E  T  L  A  M  W  T  P  T  I  P  F  S  V  Q  E  H  L  Q  Q  Q  D  S  R  I  S  L  R  *       1130

CCAGCTGTGCTCTGGACAGGCATGTTCTCTGAGGACACTAACCACGCTGGACCTTGAACTGTTGGACACAGCTCTTCTCCAGG           3600

CTGTATCCCATGAGGCCTCAGCATCCTGGCACCCCGGCCTCCTGGTTCAGGGTTGGCCCCTGCCGGCTGCGGAATGAACCACATCTTG       3690

CTCTGCTGACAGACACAGGCCCGGCTCCTTTAGCGCCAGGCTCCCAGGCTGGGATGCTGGTGGCAGCTGCGGTCCACCCAGGAGCCC        3780

CGAGGCCTTCTCTGAAGGACATTGCGGACAGCCACGGCCAGGCCAGAGGGAGTGACAGAGGCAGCCCCCATTCTGCCTGCCAGGCCCCTG     3870

CCACCCCTGGGGAGAAAGTACTTCTTTTTTTATTTTTAGACAGAGTCTCACTGTTGCCCAGGCTGGCGTGCAGTGGTGCGATCTGGGTT      3960

CACTGCAACCTCCGCCTCTTGGGTTCAAGCGATTCTTCTGCTTCAGCCTCCCGAGTAGCTGGGACTACAGGCACCCACCATCATGTCTGG    4050

CTAATTTTCATTTTTAGTAGAGACAGGGTTTTGCCATGTTGGCCAGGCTGGTCTCAAACTCTTGACCTCAGGTGATCCACCCACCTCAG    4140
```

FIG. 3e

```
CCTCCCAAAGTGCTGGGGATTACAAGCGTGAGCCACTGCACCGGGCCACAGAGAAAGTACTTCTCCACCCTGCTCTCCGACCAGACACCT   4230
TGACAGGGCACACCGGGCACTCAGAAGACACTGATGGGCAACCCCCAGCCTGCTAATTCCCCAGATTGCAACAGGCTGGGCTTCAGTGGC   4320
AGGCTGCTTTTGTCTATGGGACTCAATGCACTGACATTGTTGGCCAAAGCTAGGCCTGGCCAGATGCACCAGGCCCTTAGCAGG         4410
GAAACAGCTAATGGGACACTAATGGGCGGTGAGAGGGGAACAGACTGGAAGCACAGCTTCATTTCCTGTGTCTTTTTTCACTACATTAT    4500
AAATGTCTCTTTAATGTCACAAAAAAAAAAAAAAAAAAAA                                                    4534
```

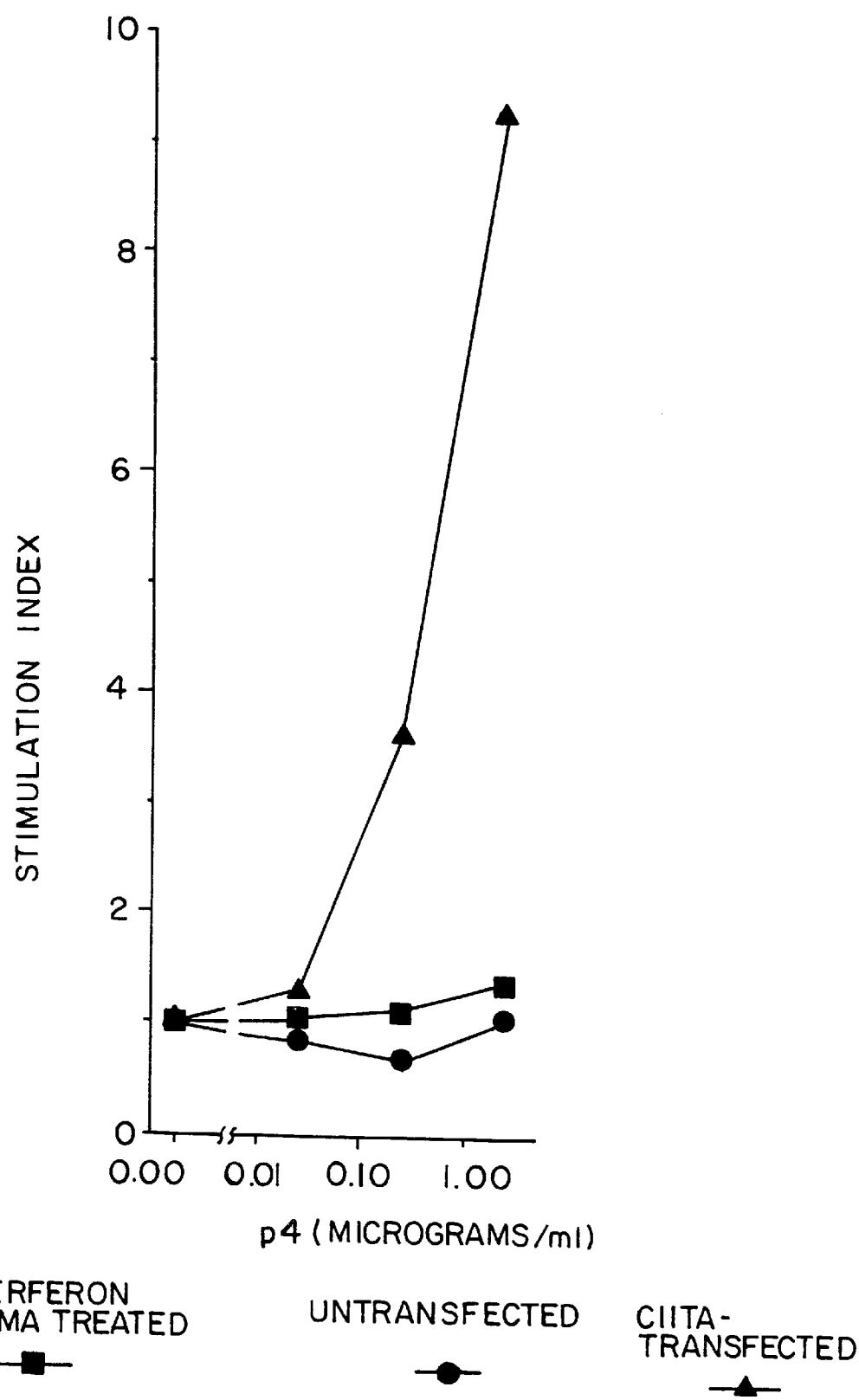

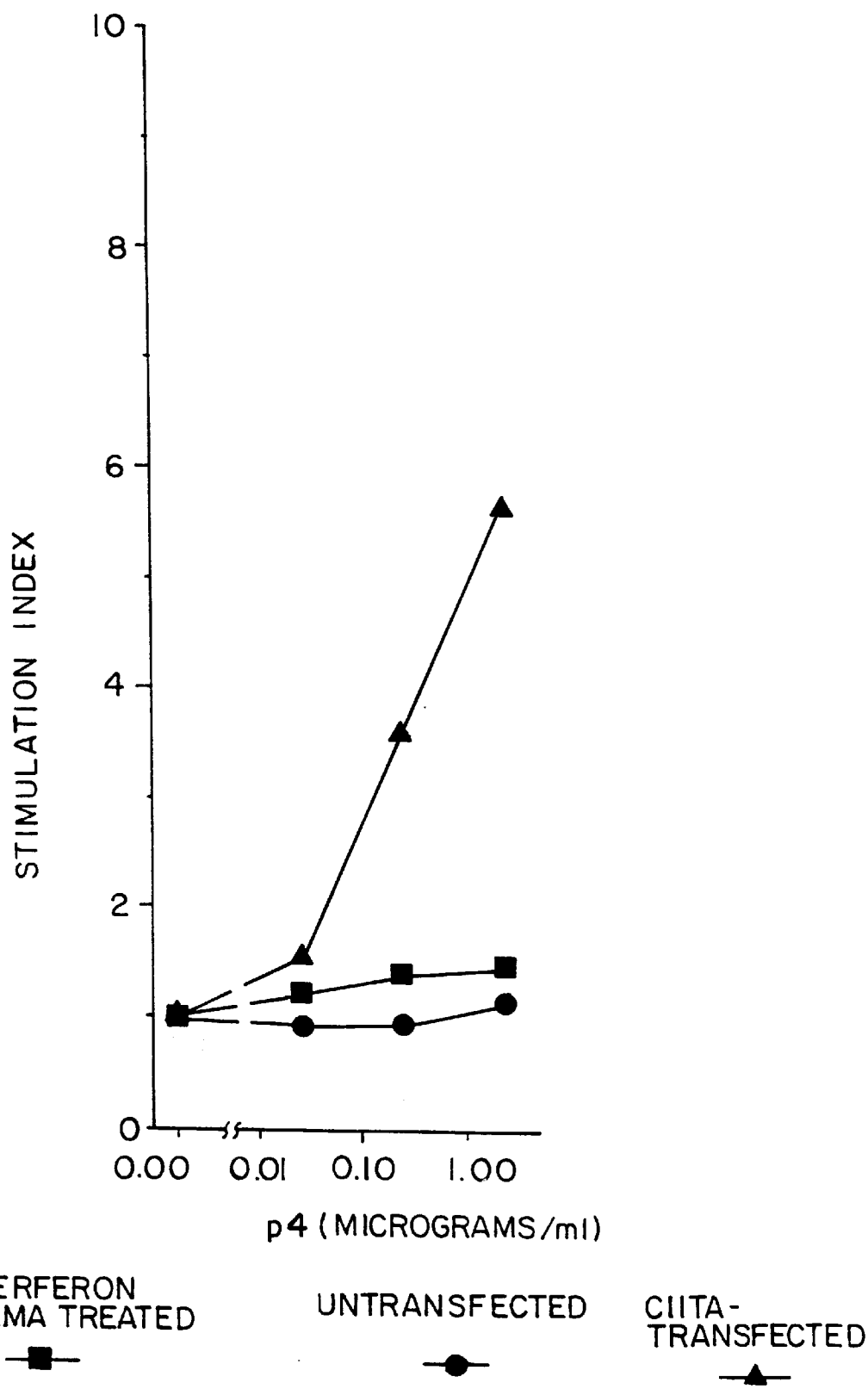

METHODS FOR THE IDENTIFICATION OF INHIBITORS WHICH SUPPRESS THE ACTIVITY OF PROTEINS DISPLAYING CIITA ACTIVITY

The invention relates to inhibitors suppressing the activity of transacting proteins which are essential for the general control of vertebrate MHC class II gene expression and methods for identifying the same. The invention additionally relates to pharmaceutical compositions containing said inhibitors, preferably for the treatment of diseases which are associated with an aberrant expression of MHC class II genes.

Class II major histocompatibility (MHC) antigens are heterodimeric transmembrane glycoproteins. Their expression at the surface of antigen-presenting cells is essential for the recognition of foreign antigens by the T cell receptor. T cell activation and antigen presentation depend on the level of expression of class II antigens on individual cells. Regulation of expression of class II genes is therefore an important aspect of the control of both normal and abnormal immune responses.

In humans, the genes encoding the a and b chains of the HLA-DP, HLA-DQ and HLA-DR class II molecules are clustered in the D region of the MHC on chromosome 6. These genes are subjected to tight and complex regulatory controls. Their expression is generally coordinated, and restricted primarily to cells of the immune system such as B lymphocytes, activated T lymphocytes, macrophages, dendritic cells, and certain specialised cells such as Kupffer cells and Langerhans cells. In certain class II negative cells, expression can be induced by stimulation with lymphokines such as interferon gamma or interleukin 4.

MHC class II genes represent a particularly complex case of regulated gene expression. Since presentation of foreign antigens to helper T cells as well as thymic education of T lymphocytes require normal expression of MHC class II molecules, the regulation of these genes is essential for a normally functioning immune system. Genes encoding MHC class II antigens were indeed initially described as "immune response genes" [Benaceraff, Science 212 (1981), 1229–1238]. This regulation concerns not only the level of expression of class II molecules but also the very restricted cell type specificity, since most cells in the body are normally MHC class II negative. The complexity of this regulation involves two distinct modes of control, namely constitutive expression in cells such as B lymphocytes and inducible expression in certain cell types, such as monocytes or fibroblasts. Finally, this family of genes encodes the a and b chains of three different HLA class II isotypes and is generally regulated in a global manner.

A number of protein factors have been shown to be capable of binding in vitro to functionally essential sequence motifs in MHC class II promoters, in particular to the conserved X and Y boxes [Glimcher et al., Ann. Rev. Immunol. 10 (1992), 13–49]. In addition, the state of occupancy of class II promoters has been analyzed in vivo [Kara et al., Science 252 (1991), 709–712].

Previously, the present inventor have isolated and identified a protein essential for the expression of MHC class II genes (transactivator of MHC class II gene expression, CIITA) and, furthermore, isolated the gene encoding said protein (Steimle et al, CELL 75 (1993), 135–146).

The CIITA proteins and the corresponding gene can be obtained by the following approach:

A regulatory mutant B cell line that exhibits no detectable defect in protein binding to HLA class II promoters was used for the cloning and identification of the MHC class II regulatory gene affected, using complementation of the mutant phenotype by cDNAs derived from an MHC class II positive B cell. Selection was based not only on re-expression of endogenous class II genes but also on the re-activation of an MHC class II promoter (inactive in the mutant cells) driving a gene for antibiotic resistance. Cloning sites unable to rejoin upon ligation were created to ensure the efficiency of a large cDNA insertion. Carefully size-selected cDNA was used and the cDNA libraries that led to the successful selection of the 4.5 kb CIITA cDNA contained inserts of average sizes of more than 3.5 kb. In addition, the transfection conditions for B lymphocytes and the immuno-selection procedure for surface expression with magnetic beads were thoroughly optimized.

Cloning of CIITA cDNA by complementation of the freely available class II negative B cell line RJ2.25 has enabled the following conclusions to be drawn: CIITA is indeed the gene affected in this mutant, and deletions in the two CIITA alleles explain the absence of intact CIITA mRNA. One allele has only an internal deletion in the CIITA gene and it appears that transcriptional readthrough results in a truncated transcript. Restoration of MHC class II gene expression by CIITA cDNA establishes a functional role for this factor in the control of constitutive MHC class II expression in B lymphocytes. CIITA behaves as a transactivator of all three HLA class II isotypes, DR, DQ, and DP, and there is no evidence of locus-specific control by this factor. The DNA sequence encoding CIITA and the deduced amino acid sequence are shown in FIG. 3. CIITA is a protein of 1130 amino acids whose mRNA is expressed at a low level. Its structure is not very informative concerning its mode of action. The $NH_2$ terminal portion of the molecule has some of the attributes of certain transcription activation domains (Mitchell et al., Science 245 (1989), 371–378), in particular a region of acidic amino acids followed by three short stretches rich in proline, threonine and serine residues. Certain transcription factors have similar activation domains. A sequence corresponding to an ATP/GTP binding site was recognised around amino acids 420 to 427 and mutagenesis at those positions will be informative. Finally, there is a leucine-rich region around amino acids 979 to 1061 that shows a weak homology with the $NH_2$ terminal portion of an RNA binding protein of yeast (Traglia et al., Mol. Cell. Biol. 9 (1989), 2989–2999). Since this weak homology concerns primarily leucine residues within a leucine-rich region, it may not be indicative of evolutionary relatedness. In the absence of an obvious DNA binding domain in the CIITA sequence, one can speculate that is may function as an adapter between factors known to bind to the X and Y boxes of MHC class II promoters and the transcription machinery.

Furthermore, it was found that the transactivator CIITA not only regulates the constitutive expression of MHC class II genes in cells such as B lymphocytes, it also controls the inducible expression of these same genes in other cell types, for instance induction by interferon gamma or by TNF. It is therefore a factor involved in the general control of MHC class II gene expression. Its structure is not related to other factors.

Several autoimmune diseases, such as insulin-dependent diabetes, multiple sclerosis, rheumatoid arthritis and lupus erythematosis are thought to be due, at least in part, to aberrant expression of HLA class II antigens on cells that normally should not express them. Abnormal T cell activation then leads to the autoimmune process.

It would consequently by very desirable to be able to down-regulate the expression of MHC class II genes, for example, in order to prevent or treat autoimmune diseases or in the case of organ transplantation, especially bone marrow transplantation, and to generate MHC class II-negative animals as xenogenic organ donors. Thus, access to substances possessing the capability of down-regulating MHC class II gene expression could provide ways for the treatment of the disorders mentioned above.

Therefore, the technical problem underlying the present invention is to isolate and identify substances which are capable of suppressing the activity of proteins displaying CIITA activity and which are essential for the expression of MHC class II genes and to provide them in purified form. Furthermore, the technical problem is to provide methods for identifying substances that are capable of suppressing the activity of proteins displaying CIITA activity. In addition, it is the technical problem to provide pharmaceutical compositions containing said substances.

The above technical problem is solved by providing the embodiments of the present invention which are characterised in the claims. Inhibitors which are capable of suppressing MHC gene expression can be identified by use of a protein having CIITA activity.

Accordingly, it is an object of the present invention to provide an inhibitor capable of suppressing the activity of a protein displaying CIITA activity and being essential for the general control of MHC class II gene expression in vertebrate cells, wherein said inhibitor is obtained by the use of recombinantly produced protein having CIITA activity and being encoded by a gene being selected from:

(a) the DNA sequence shown in FIG. 3;

(b) DNA sequences which hybridise to the DNA sequence of (a);

(c) allelic derivatives or fragments of the DNA sequence of (a) or (b); or (d) DNA sequences which are degenerate as a result of the genetic code to the DNA sequence of (a), (b) or (c).

The preferred sequence encoding the protein for identifying said inhibitors is given in FIG. 3.

It will be understood that the person skilled in the art provided with the sequence shown in FIG. 3 would be in a position to use this DNA sequence, a fragment thereof, or a corresponding oligonucleotide in order to isolate related DNA sequences from genomic or cDNA libraries of vertebrates such as mammals, or from other human individuals. Related DNA sequences are for instance allelic human DNA sequences. On the other hand, the person skilled in the art, provided with the screening strategy of the present invention, shown in the Examples, would be in a position to isolate corresponding DNA sequences from other vertebrates, such as mammals, or from other human individuals. Furthermore, the DNA sequences given in FIG. 3 or DNA sequences which are related to them can be obtained by chemical synthesis. All the above DNA sequences are within the scope of the present invention. Thus, the present invention also relates to DNA sequences which hybridize to the DNA sequence of FIG. 3 under conventional hybridization conditions.

Additional preferred sequences encoding the protein for identifying said inhibitors are DNA sequences which are related to the above DNA sequences by the degeneration of the genetic code or DNA sequences encoding a protein with the amino acid sequence shown in FIG. 3.

The recombinant production of the protein having CIITA activity for identifying the inhibitors of the present invention can be carried out by conventional methods using the DNA sequences described above for insertion into a vector.

A preferred recombinant vector is a plasmid in which the inserted gene is in operable linkage with an expression control sequence. Another preferred recombinant vector is pDVP10-1, containing a 4543 bp cDNA-insert in plasmid vector DV which encodes the human MHC class II transactivator. This cDNA was synthesised from mRNA of the HLA class II positive parental B cell line Raji. This plasmid was deposited on Jul. 19, 1993 as a strain of *Escherichia coli* (*E. coli* pDVP10-1) containing the plasmid. The accession number if DMS 8422.

Host organisms useful for the recombinant production of biologically active CIITA can be selected by the person skilled in the art. Such host organisms are preferably bacteria such as *E. coli* or *Bacillus subtilis,* yeast such as species or strains of Saccharomyces (e.g. *Saccharomyces cerevisiae*), and other eukaryotic host cells such as insect or mammalian cells.

The transformed host organism of the present invention is cultivated under suitable conditions in a culture medium and the resulting expression product is recovered from the medium. Optionally, the recovered expression product can be purified according to conventional methods, such as chromatographies using ion exchange resins or affinity chromatography material, for example, monoclonal or polyclonal antibodies attached to a matrix.

The inhibitors of the present invention can be identified by preparing a test mixture, wherein the inhibitor candidate is incubated with the protein having CIITA activity under appropriate conditions that allow the protein to be in an native conformation. Such an in vitro test system can be established according to methods well known in the art. Inhibitors of proteins that display CIITA activity could be identified, for example, by first screening for either synthetic or naturally occurring molecules that bind to the recombinant CIITA protein and then, in a second step, by testing those selected molecules in cellular assays, testing for inhibition of CIITA, as reflected by inhibition of MHC class II expression.

Screening for molecules that bind to recombinant CIITA could easily be performed on a large scale, screening for very large numbers of candidate molecules from "libraries" of synthetic and natural molecules. Binding could be detected, among other assays, as fine changes in the structure and/or size of recombinant CIITA upon binding to other molecules, as detected by state of the art protein chemistry assays. These include fluorescence anisotropy (G. Turcatti et al., Biochemistry, 34:3972–3980, 1995) and surface plasmon resonance (SPR) (D. J. O'Shannessey et al., Methods in Enzymology, 240:323–349, 1994, A. C. Greenlund, Immunity, 2:677–687, 1995). SPR can be performed with either CIITA immobilised or the candidate inhibitor molecules immobilised on the appropriate support. SPR can also be performed with great sensitivity as a competition assay (R. Karlsson, Anal. Biochem., 221:142–151, 1994).

In a second step, cell-based assays for CIITA inhibition will rely on both CIITA negative mutant B cell lines (such as RJ2.25 or RM3), stably transfected with CIITA cDNA under the control of a constitutive promoter and/or on MHC class II-negative cell lines, such as HeLa cells, also stably transfected with CIITA cDNA. The assay will rely on the inhibition of cell surface expression of HLA-DR molecules, measured by standard immunofluorescence. Such stable transfectants, as mentioned above, have been generated in our laboratory as tools for cell-based assays of CIITA inhibitors.

Alternatively, identification of such molecules can be carried out using an in vivo test system on the basis of the experiments described in Examples 2, 6 and 7. Preferably, a human cell of a HLA class II negative mutant cell line (e.g. RJ2.25, RM3 or REM-34 described in Example 2, below) comprising a plasmid which allows the expression of the protein having CIITA activity is contacted with the inhibitor candidate and then the level of expression of HLA class II genes is compared with that of a control cell which has not been contacted with the inhibitor candidate. Determination of expression of HLA class II genes can be carried out as described in Example 2, below.

Preferably, the inhibitor of the present invention inhibits the interaction of the protein displaying CIITA activity with control sequences of MHC class II genes, thereby causing down-regulation of the expression of said genes.

A further object of the present invention are inhibitors which are designed on the basis of the three dimensional structure of CIITA, information that can be obtained from recombinant CIITA using state of the art technology, for example, x-ray structure analysis, spectroscopic methods etc.

A still further object of the present invention is an inhibitor which is a synthetic organic chemical, a natural fermentation product, a substance extracted from a microorganism, plant or animal, or a peptide. Such inhibitors candidates can be screened by use of the test systems described above.

In addition, inhibitors which bind to the ATP-binding site of the protein displaying CIITA activity or to its N-terminal acidic activation domain can be used for suppressing the activity of proteins displaying CIITA activity. Such inhibitors can be also screened by the test systems described above, wherein the site of binding of the inhibitor to the protein is determined or wherein a fragment of the protein displaying CIITA activity is used which comprises said binding site. Such fragments can be generated, for example, on the basis of the sequence shown in FIG. 3: The N-terminal region of acidic amino acids, which might correspond to the transcription activation domain is followed by three short stretches rich in proline, threonine and serine residues, the amino acid sequences around amino acids 420 to 427 might correspond to the ATP-binding site.

A further object of the present invention is the use of a recombinantly produced protein having CIITA activity and being encoded by the gene defined in claim 1 or having the amino acid sequence as shown in FIG. 3 for the identification of an inhibitor that is capable of suppressing the activity of a protein displaying CIITA activity.

A further object of the present invention is a method for identifying an inhibitor that is capable of suppressing the activity of a protein displaying CIITA activity, wherein said method comprises the screening for said inhibitor by exploiting its capability to bind to the protein displaying CIITA activity under appropriate conditions.

For such use of the protein having CIITA activity or for such method the in vitro—or in vivo—test system described above is preferred. Preferably, inhibitors are identified, which bind to the ATP-binding site or to the N-terminal acidic activation domain of the protein displaying CIITA, e.g. by assaying inhibitor candidates with fragments of the CIITA protein as described above.

A still further object of the present invention is a method for identifying an inhibitor that is capable of suppressing the activity of a protein displaying CIITA activity, wherein said method comprises designing appropriate inhibitors on the basis of the three dimensional structure of the recombinant CIITA protein. Preferably, the test systems described above are used in such a method.

Still a further object of the present invention is a pharmaceutical composition which contains the inhibitor of the present invention. This pharmaceutical composition optionally also contains pharmaceutically acceptable carriers and/or additives. The dosage depends on the condition of the patient and the symptoms of the disease.

Preferably, the pharmaceutical composition of the present invention which contains the above-mentioned inhibitor can be used for the treatment of diseases wherein a decrease of the level of the expression of MHC class II genes is desirable or for the generation of MHC class II negative transgenic animals as a source of organs for xenogenic transplantation or of cells for universal cell transplants. Among other things, these include autoimmune diseases wherein an aberrant and excessive expression of HLA class II molecules at the surface of certain cells is thought to be responsible for the autoimmune pathological processes. These include insulin dependent diabetes (IDD), multiple sclerosis (MS), lupus erythematosis (LE) and rheumatoid arthritis (RA). The aberrant expression of MHC class II genes and proteins has been documented in certain animal models of these diseases. Furthermore, animal models of some of these autoimmune diseases have been treated successfully with antibodies directed against MHC class II molecules, pointing to the desirability of down-regulation of the expression of MHC class II genes in autoimmune diseases.

Finally, the present invention relates to a pharmaceutical composition comprising the inhibitor of the invention for determining whether a disease associated with an aberrant expression of a MHC class II gene is caused by the presence of abnormal amounts of the protein having CIITA activity or by other factors. For example, if cells of a patient having a disease characterized by reduced or eliminated expression of a MHC class II gene do not show a positive response in presence of said inhibitor in an assay system, e.g. as described above, one could conclude that the disease is not caused by the presence of abnormal amounts of the CIITA protein, but for example, a cis-acting mutation in the MHC class II gene itself. Based on such a result, the therapy could be appropriately adapted.

(a) Vector EBO-Sfi contains the hygromycin resistance gene (hygr-76) from plasmid pTG76 [Giordano et al., Gene 88 (1990), 285–288]. The cDNA cloning cassette consists of two inverted SfiI sites separated by a bacterial chloramphenicol acetyl transferase gene (SfiI-CAT-gene-SfiI). Cloned cDNAs are driven by the simian virus 40 early (SV40e) promoter and polyadenylation signal (Poly-A). Open boxes indicate the EBV origin of replication (ORI P), the EBV nuclear antigen gene 1 (EBNA-1) under the control of the simian virus 40 late promoter (SV40l) and the bacterial ampicillin resistance gene (amp).

(b) Vector DRA-CD was generated from EBO-Sfi by insertion of a cD4 cDNA [Maddon et al., Cell 42 (1985), 93–104] under control of the 300 bp HLA DRA promoter and a 130 bp polyadenylation signal into the unique HindIII site of EBO-Sfi.

(c) For generation of vector DV the SV40 early promoter driving the hygr-76 gene was replaced by the 300 bp HLA DRA promoter via the unique HindIII and BglII sites.

Figures 2, 2A:
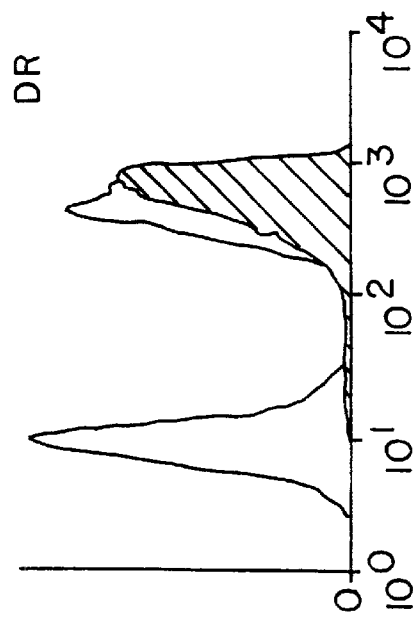
Figures 2, 2A, 3, 4:
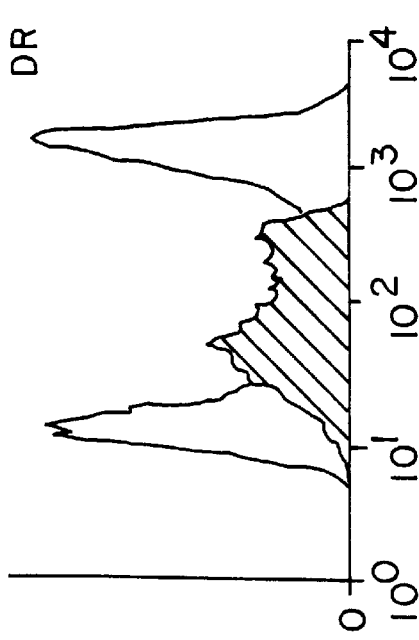
Figures 1, 2A:
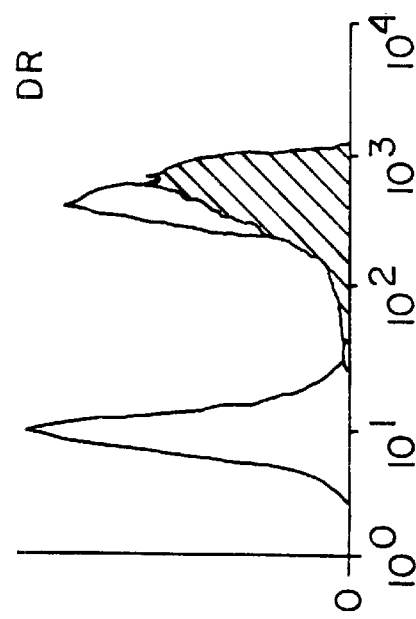
FIGS. 1A–1C . Restriction map of the EBO-Sfi and derived cDNA expression vectors DRA-CD and DV.
Figures 2, 2A, 3:
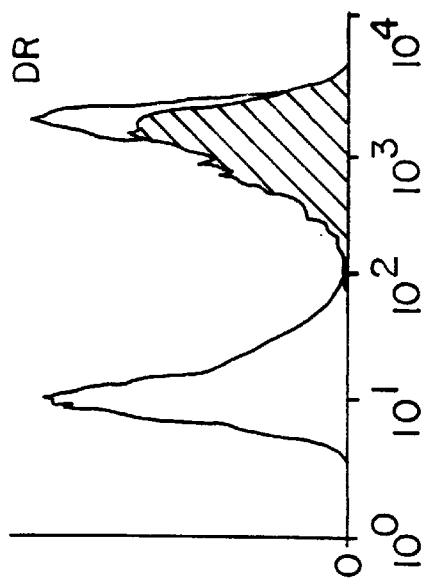
Figures 1, 2B:
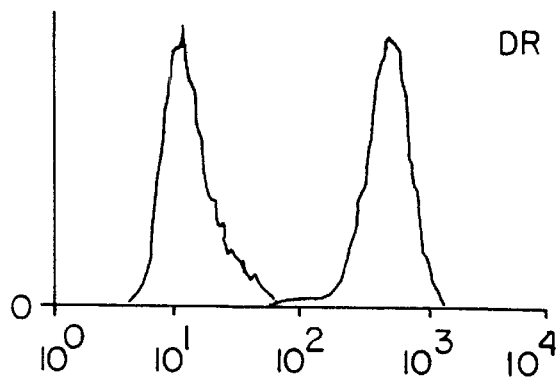
Figures 2, 2B:
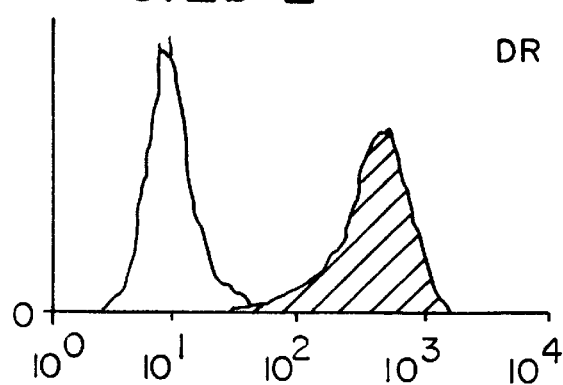
Figures 2, 2B, 3:
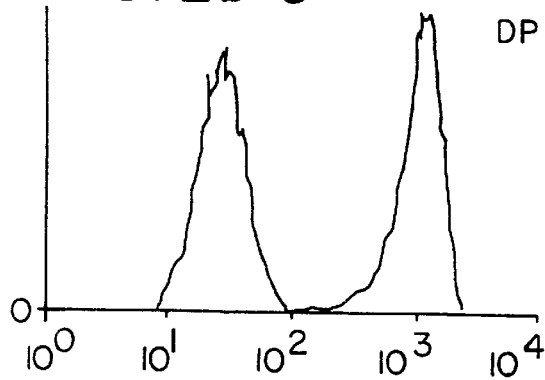
Figures 2, 2B, 3, 4:
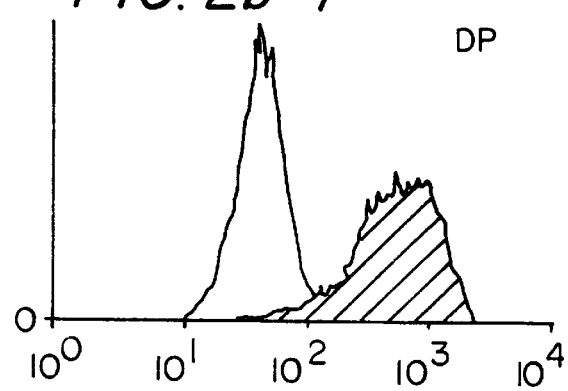
Figures 2, 2B, 3, 4, 5:
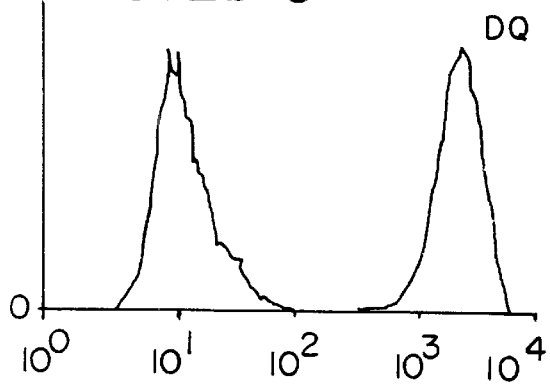

FIGS. 2A and 2B. Isolation of CIITA cDNA by expression cloning and correction of HLA class II expression in RJ2.25 cells.

(a) Selection of HLA-DR positive cells. RJ2.25 cells transfected with plasmid DNA from DV-pools DVP6, −7 and −10 (panels 1 to 3) and one DRA-CD pool (DRA-CDP1, panel 4) were selected for Hygromycin B resistance and sorted twice (DV transfectants) or three times (DRA-CD transfectants) with the HLA DR specific antibody 2.06 and magnetic beads. The sorted populations were stained with the HLA DR antibody L243 and analyzed by FACS (shaded profiles). As negative and positive controls, RJ2.25 and Raji cells were analyzed in the same way (open profiles).

(b) CIITA cDNA restores expression of all three HLA class II isotypes. RJ2.25 and Raji cells (panels 1, 3, 5) or RJ2.25 cell transfected with DRA-CD and DRA-CD/CIITA (open and shaded profiles in panels 2, 4, 6) were stained with antibodies specific for HLA DR (L243; panels 1, 2), —DP (B7/21; panels 3, 4) and —DQ Tü22; panels 5, 6) and analyzed by FACS (Fluorescence Activated Cell Sorter).

FIG. 3. Nucleotide and predicted amino acid sequence of the CIITA cDNA.

The complete nucleotide sequence of cDNA clone pDVP10-1 and the deduced amino acid sequence of CIITA are shown. The 5' ends of three independent clones are indicated by "#", the upstream in-frame stop codon and the stop-codon at nt position 3506 are indicated by "*". The N-terminal regions rich in glutamate/aspartate (marked "acidic") and the stretches rich in proline/serine/threonine (marked "I, II, III") are overline. The ATP/GTP binding cassette is double underlined. The Alu-repeat and the polyadenylation signal in the 3' untranslated region are underlined. Numerous potential protein kinase C and casein kinase II sites (13 and 15) are present in the sequence but not indicated in the figure.

Figure 4A:
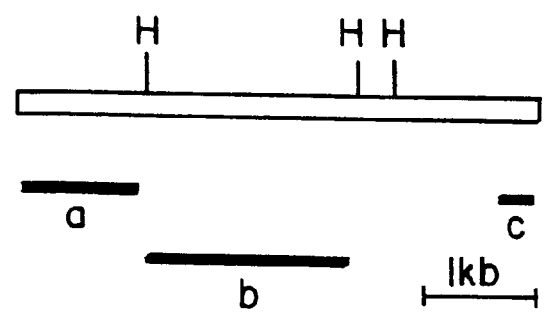
Figure 4B:
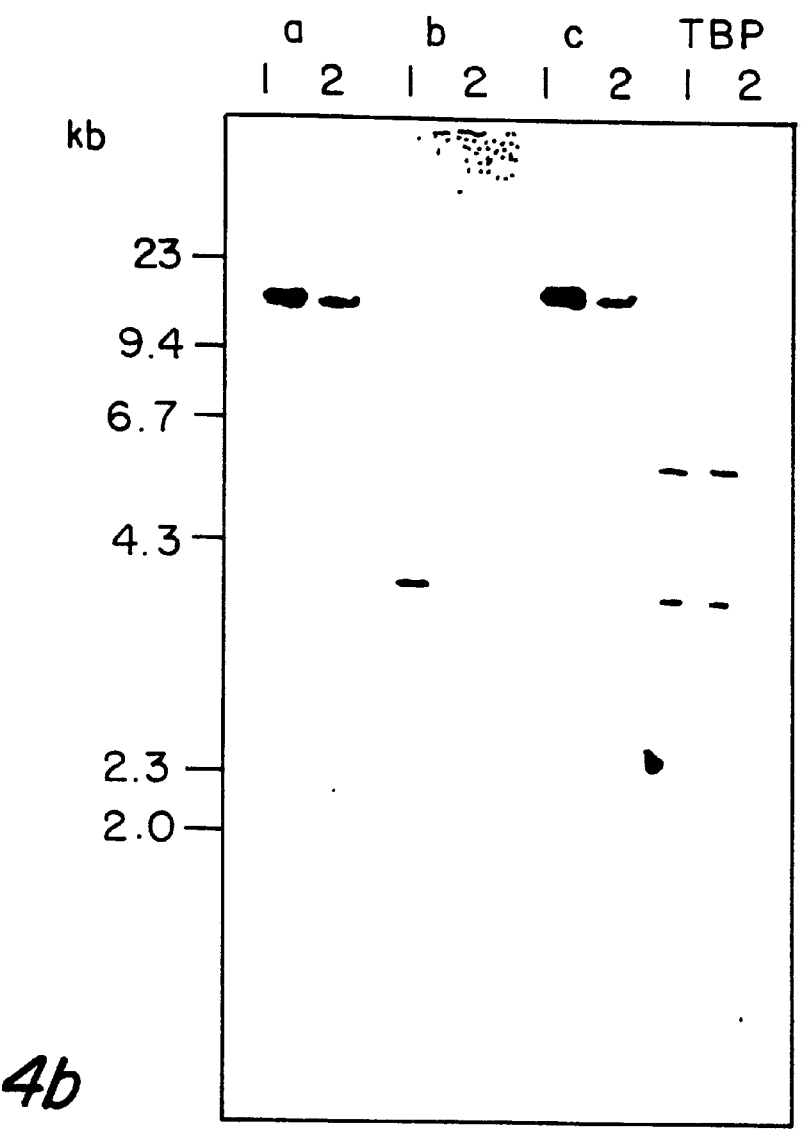

FIGS. 4A and 4B. Evidence for deletion in the CIITA gene in mutant cell line RJ2.25.

(a) Schematic representation of the CIITA cDNA with its three internal HindIII sites (H). The three fragments of the CIITA cDNA used as Southern hybridization probes are indicated by filled bars.

(b) 10 μg of genomic DNA were digested with HindIII, fractionated in a 0.7% agarose gel, denatured, transferred and hybridized to CIITA- or TBP-specific probes. Two identical filters were prepared with DNA from Raji (lane 1) and RJ2.25 (lane 2). The first filter was hybridized to a 1.1 kb HindIII probe from the 5' end of CIITA (probe A). After stripping, the same filter was rehybridized to probe B, the central 1.8 kb HindIII fragment of CIITA cDNA. The second filter was first hybridized to probe C spanning nucleotides 4152 to 4520 of CIITA. To confirm equal quantities of DNA in both lanes this filter was then stripped and rehybridized to a probe from the 3' end of human TBP cDNA [Keo et al., Science 248 (1990), 1646–1650]. The CIITA specific bands show lengths of 13 kb, 3.8 kb and 14 kb for probes A, B and C, respectively.

Figure 5A:
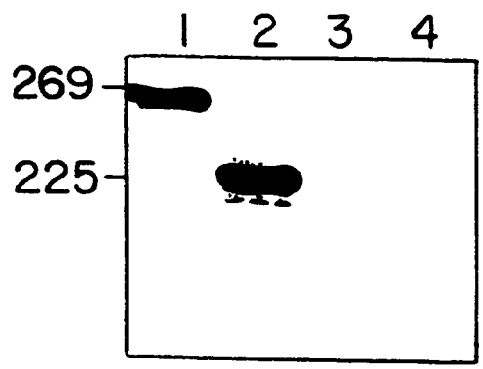
Figure 5B:
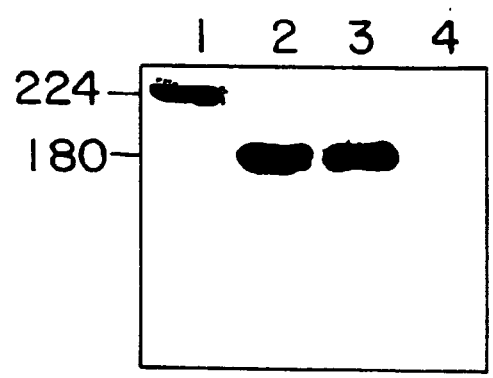
Figure 5C:
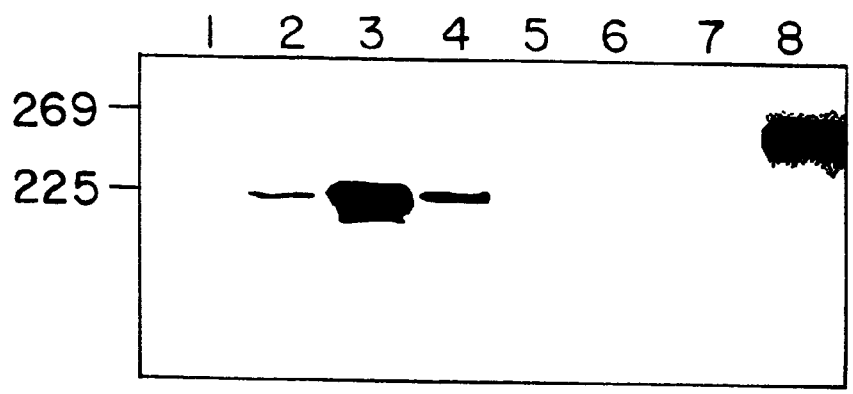
Figures 2, 6:
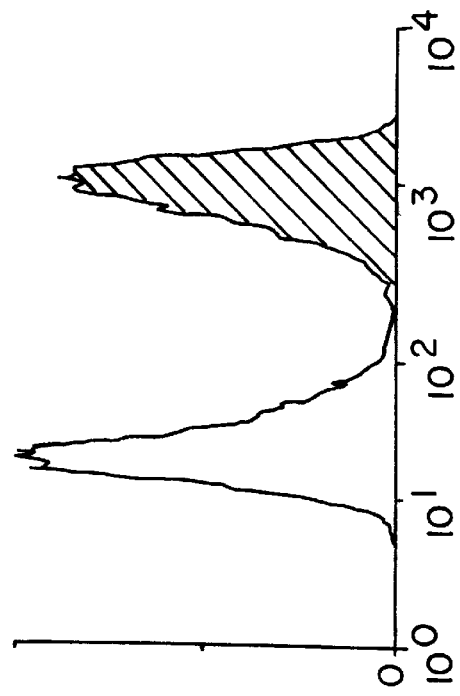
Figures 4, 6:
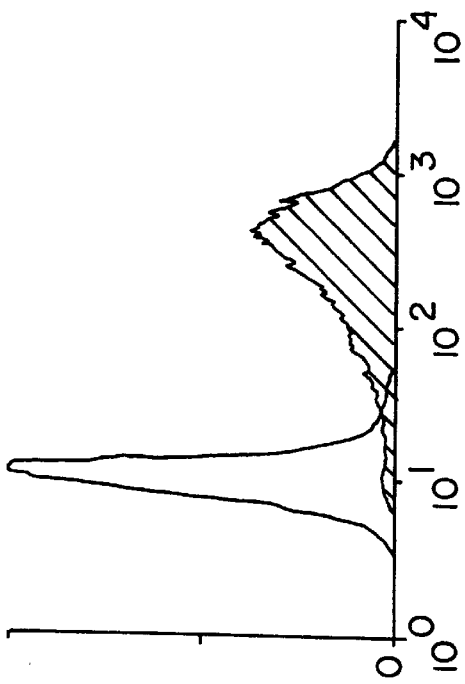
Figures 1, 6:
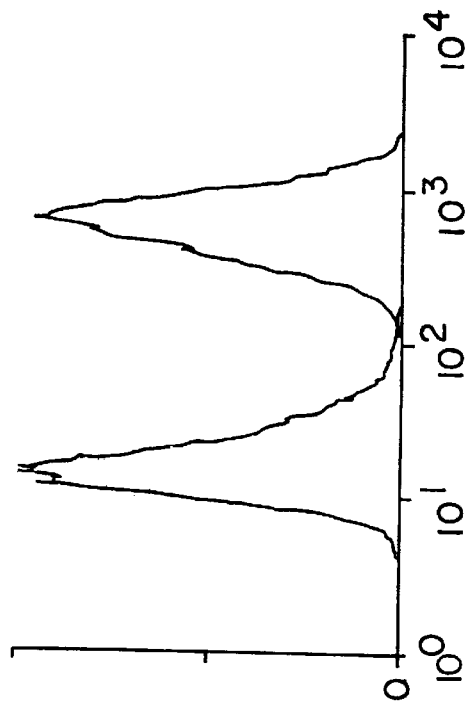
Figures 3, 6:
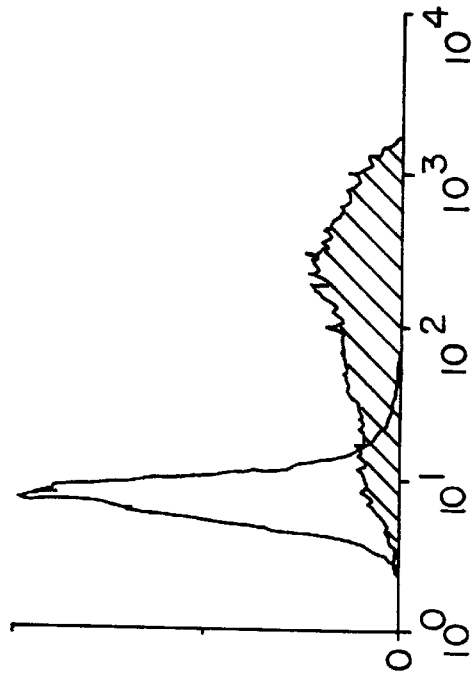

FIGS. 5A–5C. RNAse protection analysis of CIITA expression. 10 μg of total RNA were hybridized in 80% formamide to 500,000 cpm of probe. Protected probe was resolved on denaturing 6% polyacrylamide gels.

(a, b) Total RNA of Raji (lane 2) and RJ2.25 (lane 3) was hybridized to riboprobes complementary to nucleotides 2049 to 1824 (a) and nucleotides 4520 to 4340 (b) of CIITA respectively. Undigested probed and yeast RNA control are shown in lanes 1 and 4.

(c) Total RNA from various cell lines was hybridized to the same central CIITA probe used in (a). 1, yeast control; 2, CO115 colon carcinoma; 3, 4, Mann, QBL B-LCLs; 5, 2102Ep teratocarcinoma; 6, MOLT4 T-lymphoma; 7, SK-N-AS neuroblastoma; 8, undigested probe. RNA quantity and quality was controlled by hybridization to a TBP specific probe (not shown).

Figures 2, 2B, 3, 4, 5, 6:
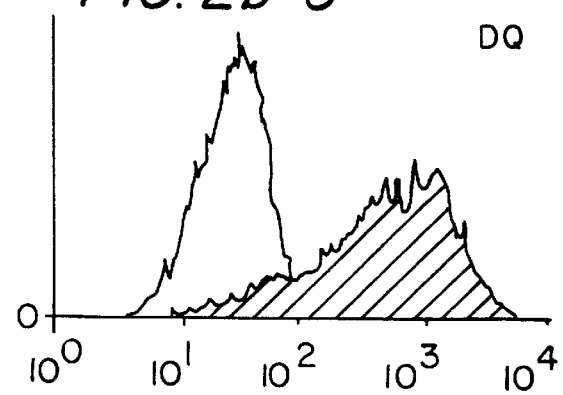

FIG. 6. CIITA cDNA corrects three different HLA class II negative mutant cell lines.

RJ2.25 (panel 2), RM3(panel 3) or REM-34 (panel 4) cells were transfected with CIITA cDNA, cloned into EBO-Sfi (shaded profiles) or with EBO-Sfi alone (open profiles). Analysis for surface HLA DR expression by FACS with L243 antibody was performed after two weeks (RJ2.25, RM3) or only five days (REM-34) of Hygromycin B selection. Panel 1 shows negative (RJ2.25; EBO-Sfi transfected) and positive (Raji) controls.

Figures 1, 7:
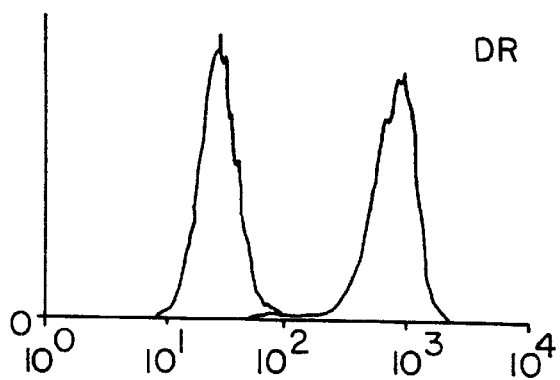
Figures 2, 7:
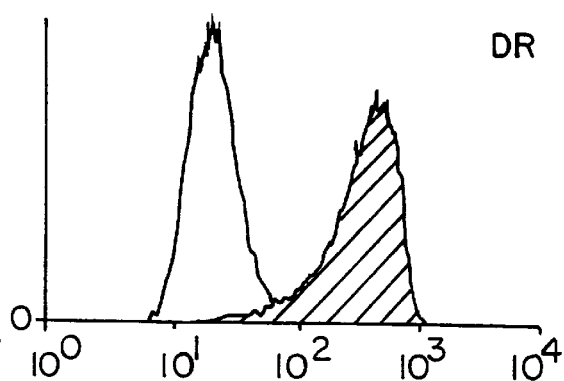
Figures 3, 7:
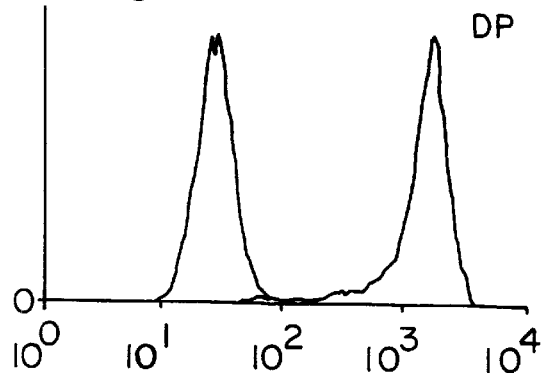
Figures 4, 7:
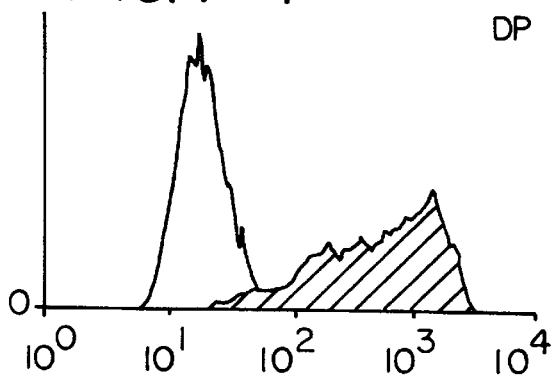
Figures 5, 7:
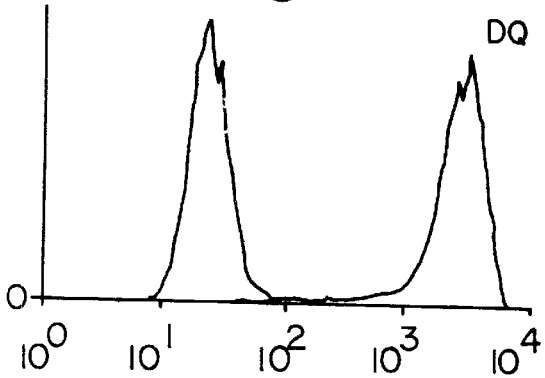
Figures 6, 7:
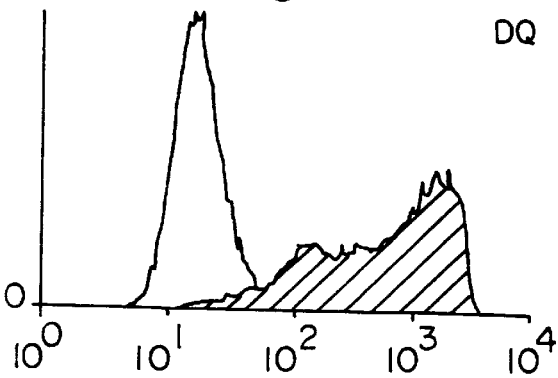

FIG. 7. CIITA cDNA fully corrects HLA class II expression on B lymphocytes from HLA class II deficient patients.

B lymphocytes from patient BLS1 were transfected with CIITA cDNA. Following selection in Hygromycin, cells were analyzed for surface expression of HLA-DR, —DP and —DQ.

Figure 8A:
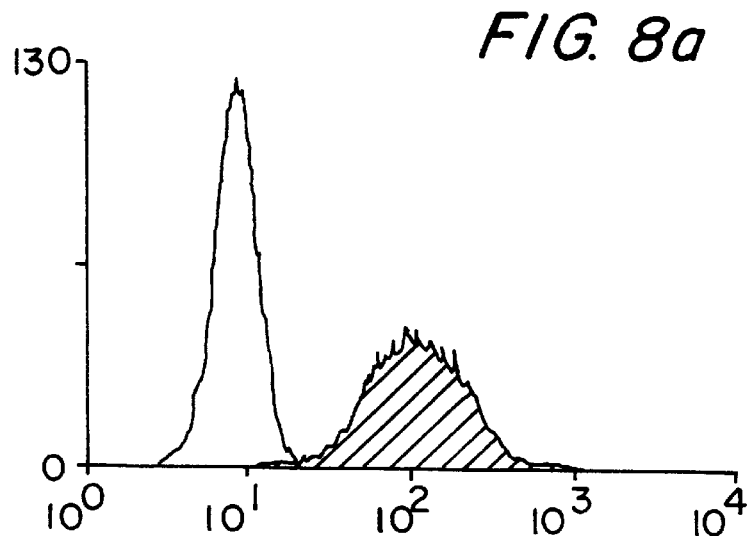
Figure 8B:
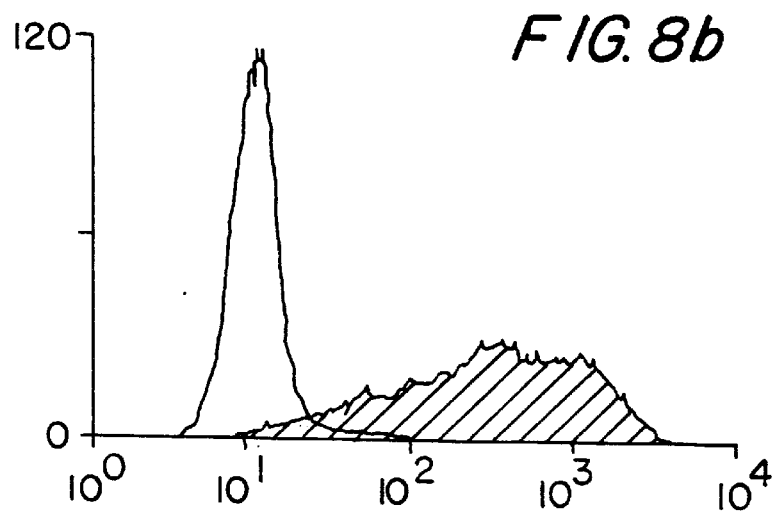
Figure 8C:
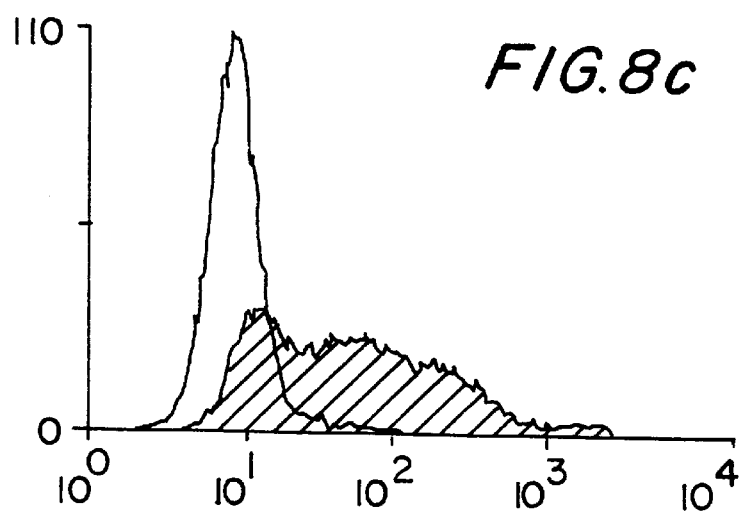

FIGS. 8A–8C. The CIITA gene induces expression of MHC class II genes in class II negative cells.

Three types of MHC class II negative cells were transfected with CIITA cDNA. Following selection in Hygromycin, cells were analyzed for surface expression of HLA-DR molecules.

A. A melanoma cell line. B. A fibroblastic cell line, 140B. C. HeLa cells

FIG. 9. Activation of human T cell clones with CIITA transfectants and interferon-stimulated cells used as APC's. Three types of cells were tested as APC'S: Untransfected melanoma cell line, MHC class II negative (●); The same cell line following 48 hours of exposure to 200 μg/ml of interferon gamma, MHC class II positive (■); The same cell line previously transfected with CIITA cDNA; MHC class II positive (▲). These cells were treated with various concentrations of p4, a tetanus toxoid peptide, at the concentrations indicated, fixed by UV light and incubated with two different human T cell clones specific for that peptide, T-50 and T-87. The extent of T cell activation was measured by incorporation of $H^3$-thymidine in a standard assay, and expressed as "stimulation index".

The invention is illustrated by the following examples:

EXAMPLE 1

Expression cloning by complementation of mutant RJ2.25

Expression cloning by genetic complementation of the class II regulatory mutant RJ2.25 implies no bias as to the nature of the genetic defect but requires that the defect concern a single gene. In addition to using re-expression of the endogenous HLA class II genes as a selection marker, the inventors constructed a series of cDNA expression vectors that allowed several different selection strategies, either separately or in combination.

Construction of the cDNA expression vector EBO-Sfi

The cDNA expression vector EBO-Sfi (FIG. 1) was constructed in the following way. The Hygromycin B resistance-conferring gene hph of EBO-pLPP [Spickofsky et al., DNA Prot. Engin. Techn. 2 (1990), 14–18 (gift of Dr. R. F. Margolskee)] was replaced by the optimized hph gene of pTG76 [Giordano et al., loc. cit. (gift of Dr. W. T. McAllister)]. The hph-76 gene under the control of the SV40 early promoter was isolated from pTG76 as a 2,546 bp fragment resulting from partial PstI and complete BamHI digestion (positions 1845 and 4391 in pTG76). From EBO-pLPP a 6,675 bp PstI-EcoRV, (positions 1859, 5765) and a 615 bp BamHI-EcoRV fragment (positions 5141, 5756) were isolated and ligated with the hph-76 PstI-BamHI fragment. In the resulting vector the SfiI sites in both SV40 early promoters were destroyed by SfiI-digestion, 3' overhang removal and re-ligation; this did not affect the promoter activity. Next, the EBO-pLPP polylinker (SacI to KpnI, positions 1 to 37 in EBO-pLPP) was replaced by a SfiI-cDNA cloning cassette. For this an 800 bp bacterial chloramphenicol acetyl transferase (CAT) gene was inserted into the SacI and KpnI sites with the help of oligonucleotide adaptors. In the resulting EBO-Sfi vector the sequences constituting the cDNA cloning cassette are as follows: 5' GAGCTCGGCCTCACTGGCC-CAT-gene-GGCCAGTGAGGCCGGTACC 3' (SEQ ID NO: 1, SEQ ID NO: 2).

Construction of the vectors DV and DRA-CD

Vector DV (FIG. 1C) was generated by replacing the hph-76 gene controlling SV40 early promoter between the unique HindIII and BglII sits in EBO-Sfi with a 300 bp fragment of the HLA DRA promoter (position −270 to position +30; relative to the transcription start site).

In vector DV, the Hygromycin B resistance gene is placed under the control of the HLA-DRA promoter. This allows antibiotic selection for reactivation of HLA class II transcription.

For the construction of DRA-CD (FIG. 1B) a reporter gene cassette consisting of the 300 bp HLA DRA promoter, the 1,742 bp human CD4 cDNA gene [Maddon et al., loc. cit.] and the 134 bp SmaI-BamHI poly-adenylation signal of pTG76 was inserted into the HindIII site of EBO-Sfi. For cDNA cloning, plasmid DNA was digested to completion with SfiI and separated from the CAT-stuffer on a 5%–20% sucrose gradient.

Construction of cDNA library and plasmid pools

Double-stranded cDNA was synthesized from 20 $\mu$g of polyadenylated mRNA prepared from Raji cells with Superscript reverse transcriptase (Gibco-BRL). The cDNA was ligated to non-palindromic SfiI-SalI adaptors (5'pTGGCCGTCGACTAC [SEQ ID NO: 3], 5'pGTAGTC-GACGGCCAGTG [SEQ ID NO: 4]). Adaptor-ligated cDNA was size-fractioned on a 5%–20% sucrose gradient and inserts greater than 2.5 kb were ligated into the plasmid vectors DV and DRA-CD, respectively. The ligation reactions were electroporated into *Escherichia coli* strain DH5A, yielding a potential library titer of more than $5 \times 10^7$ recombinants for this size fraction. The mean insert size of cDNAs after SalI or SfiI digestion was approximately 3–3.5 kb. Recombinants were plated out at $5 \times 10^4$ colonies per 15 cm petri dish with Luria-broth agar containing 50 $\mu$g/ml ampicillin. Cells were scraped off the plates in pools of $5 \times 10^5$ recombinants and were partially stored as glycerol stocks at −70° C., the remaining bacteria being used to isolate plasmid DNA by the alkaline lysis miniprep method [Sambrook et al., Molecular Cloning, A Laboratory Manual, Cold Spring Harbor Laboratory Press (1989)].

RJ2.25 transfections

Cells were grown in an RPMI 1640 medium supplemented with 10% fetal calf serum, penicillin, streptomycin, and glutamine at 37° C. in 5% $CO_2$.

RJ2.25 were recloned by limiting dilution before the transfection experiments. Fifty million RJ2.25 cells were transfected by electroporation with 20 ul of plasmid DNA and 400 ug *E. coli* tRNA as carrier in 800 ul RPMI medium. One ml of FCS was added to each electroporation cuvette immediately after delivery of the electric pulse. Forty-eight hours after transfection, Hygromycin B (Calbiochem) was added at 125 ug/ml; the dose was increased by two steps in three day intervals to a final concentration of 250 ug/ml. Cell numbers were kept between $1 \times 10^5$ and $1 \times 10^6$/ml. Hygromycin B selection was complete after two weeks. Transfection efficiencies as determined by limiting dilution experiments were routinely greater than 25% stable transfectants with EBO-Sfi and DRA-CO plasmids. DV-plasmids yielded 10%–15% stable transfectants when transfected into Raji cells; after transfection into RJ2.25 greater, 99.9% of the cells died under Hygromycin B selection.

Flow cytometric analyses

The following HLA class II specific monoclonal antibodies were used: 2.06 (DR, gift of C. Epplen), L243 (DR,), B7/21 (DP, gift of N. Reinsmoen), Tü22 (DQ, gift of A. Ziegler). IN addition, we used CD4 specific OKT4 monoclonal antibody (gift of M. Hadam).

Cells ($10^6$) were incubated in staining buffer (phosphate-buffered saline, 1% bovine serum albumin and 2.5% heat-inactivated human AB serum) with monoclonal antibodies for 30 min at 4° C. The cells were washed and incubated with FITC-labeled rabbit anti-mouse IgG (SEROTEC). After washing, 10,000 viable cells were analyzed using a FACS can flow cytometer (Becton-Dickinson). Dead cells were excluded from the analysis by staining them with propidium iodide and by their forward and sideways light scattering properties.

Cell sorting

The transfected RJ2.25 cells were subjected to a first round of sorting three to five days after transfection. Between $3 \times 10^7$ and $1.2 \times 10^8$ cells were used per transfection and sorting step. Cells were collected by centrifugation, washed once with PBS/BSA and then stained with 2.06 or OKT4 ascites antibody in PBS/BSA in the presence of 2.5% heat-inactivated human AB-serum for 30 min. on ice. After washing, the cells were incubated with 5–10 ul goat-anti-mouse coupled magnetic beads (Dynal, Norway) in PBS/BSA supplemented with 2.5% heat-inactivated goat serum for 30 min. on ice. Bead-coupled cells were separated from unstained cells with the help of a magnet, washed several times and expanded. The beads stick for several days to the cells but do not inhibit growth and were not removed. Further rounds of selection were carried out when the cell populations had grown up to sufficient numbers ($3–5 \times 10^7$). Hygromycin B selection was maintained during this whole process, although the concentration of the antibiotic was sometimes reduced for one or two days after bead selection to optimize cell survival. The sorted populations were analyzed for HLA DR expression by staining them with 2.06 or L243 and FACS analysis after each round of selection. After two rounds of immuno-selection in addition to Hygromycin B selection, the cultures of transfectants obtained with three out of five DV-cDNA pools exhibited strong HLA-DR expression (FIG. 2A, panels 1, 2, 3).

Plasmid rescue

Plasmids were isolated from sorted cell populations by alkaline lysis in close analogy to bacterial miniprep methods. Rescued plasmid pools were transfected by electroporation into *E. coli* strain DHlOB (generous gift of Gibco-BRL). Several hundred colonies were scraped from agar plates, expanded, and plasmid DNA was extracted. Inserts of these plasmid pools were analyzed by digestion with SfiI, SalI, SacI and KpnI followed by gel electrophoresis. Plasmid DNA from randomly picked single colonies was analyzed in the same way and plasmids containing the same insert type as the one predominantly found in the rescued pools were used for retransfection into RJ2.25 cells.

Plasmid pools rescued from these highly selected populations exhibited a limited set of characteristic insert-derived bands following digestion with SalI, SfiI, SacI and KpnI and gel electrophoresis. The same 4.5 kb cDNA insert was found in over 50% of randomly picked bacterial colonies obtained with the rescued plasmids. The transfectants selected for Hygromycin B resistance only were negative when tested for HLA-DR expression. Plasmid pools rescued from these cells showed a random distribution of insert sizes.

Finally, RJ2.25 mutant cells stably transfected with cDNA libraries prepared in vector DRA-CD were sorted by immuno-selection, both for expression of HLA-DR and for CD4 expression (with 2.06 and OKT4 antibodies and magnetic beads). After three rounds of sorting, the selected transfected populations showed clear HLA-DR or CD4 expression, albeit somewhat weaker than the RJ2.25/DV pools described above (FIG. 2A, panel 4). About 30% of the plasmids rescued from the cells sorted for HLA-DR expression alone showed the same preferential 4.5 kb insert as the one found in the DV transfectants (see above). In contrast, plasmids rescued from transfectants selected for CD4 expression alone also displayed a preferential but different cDNA insert, which upon retransfection in mutant cells had no effect on HLA class II expression (not shown). These plasmids have not yet been analyzed further.

EXAMPLE 2

CIITA cDNA restores expression of a full wild type HLA class II phenotype in the mutant cell line Plasmids from individual colonies containing the 4.5 kb cDNA insert found preferentially in selected transfectants re-expressing HLA-DR (see above) were isolated and then re-transfected into class II negative mutant RJ2.25 B cells. Transfectants were then selected for Hygromycin B resistance only. Without any immuno-selection for HLA class II expression, stable transfectants expressed wild type levels of HLA-DR (FIG. 2B, panel 2). Identical results were obtained in these complementation experiments whether the Hygromycin resistance gene was driven by an SV40 promoter or by a DRA promoter. The cDNA found capable of restoring expression of HLA-DR genes in the regulatory mutant cell line was called CIITA, for "Class II transactivator."

Expression of the different HLA class II genes is generally regulated in a global fashion [Mach et al., Cold Spring Harb. Symp. Quant. Biol. 51 (1986), 67–74], although exceptions have been described. Cell surface analysis of RJ2.25 mutant cells stably transfected with CIITA cDNA showed not only expression of wild type levels of HLA-DR molecules, the class II molecules used for the initial selection of corrected cells, but also demonstrated re-expression of the HLA-DP and HLA-DQ isotypes (FIG. 2B, panel 2–4). The CIITA transactivator affected in RJ2.25 is therefore sufficient to correct for the expression of all HLA-DR, —DQ and —DP a and b chain genes and to restore in the mutant cell line a normal and complete HLA class II positive phenotype.

EXAMPLE 3

Sequence of CIITA cDNA and Protein

Double-stranded DNA was sequenced by the dideoxy chain termination method using mostly the T7 G/A-deaza sequencing kit of Pharmacia but also the Bst sequencing kit of Biorad. The cDNA and translated protein sequence were tested for homology to sequences in the EMBL (release 33), GenBank (release 74), SWISS-PROT (release 24), and dbEST databases. Sequence analysis was performed with PC/Gene release 6.7 (Intelligenetics), the BLAST server, and the PROSITE dictionary.

The nucleotide and deduced amino acid sequence of CIITA cDNA are presented in FIG. 3. The 5' ends of CIITA cDNA clones obtained from several independent sorting experiments were sequenced and their starting points are indicated in the figure. Clone pDVP10-1 was sequenced completely. It is 4,543 bp in length and contains an open reading frame of 3390 bp, coding for a predicted protein of 1130 amino acids, with a start codon at nucleotide position 116. There is a stop codon in the same reading frame at position 20–22. Although this first in-frame ATG codon (position 116) fulfills the most important criteria for a translation initiation site, a second in-frame ATG codon, at bp 188 (a.a. position 25), is in the context of a perfect "Kozak box" and may also serve as a start codon, leading to a protein of 1106 amino acids. The 1130 amino acid protein has a predicted molecular weight of 123.5 kD, which corresponds well to an apparent molecular weight of 135–140 kD observed for the protein translated in vitro from CIITA cDNA (not shown). The 5' UT region is 115 bp long and the 3' UT region is 1 kb long.

Apart from Alu-repeats in the 3' untranslated region of the CIITA cDNA (bp 3890 to 4190), no significant homologies to either nucleotide or protein sequences in available data bases were detected. A search for known or potential functional motives within the predicted CIITA protein sequence revealed a potential ATP/GTP binding site at aa position 420 to 427 (FIG. 3). The N-terminal portion of the protein shows a region rich in acidic residues (aa 30 to 160, see FIG. 3), with the sequence spanning residues 50 to 137 containing 30% glutamate/aspartate. Residues 162 to 322 are rich in proline, serine and threonine. Within this region, three stretches (residues 163–195, 209–237 and 260–322) show 20% to 23% proline and 17% to 28% serine/threonine. CIITA is therefore a novel gene whose function is essential to MHC class II gene expression in B lymphocytes.

EXAMPLE 4

Identification of the CIITA-gene defect in the mutant B cell line

Since the HLA class II negative mutant RJ2.25 was generated by low dose irradiation, which is known to induce deletions and chromosome rearrangements, we analyzed the organization of the CIITA gene in RJ2.25 by Southern blot hybridization.

High molecular weight DNA was extracted from the cultured cells [Miller et al., Nucl. Acids Res. 16 (1988), 1215]. Restriction endonuclease-digested DNA was separated on 0.7% agarose/TBE gels and capillary-transferred onto positively charged nylon membranes (Boehringer-Mannheim). Southern hybridization was carried out with random-nonamer $^{32}$p labelled cDNA fragments in Quick-hybridisation Mix (Stratagene) according to the manufacturer's instructions in the presence of sonicated single-stranded human placenta DNA as competitor. The Blots were washed twice in 2×SSC, 0.1% SDS at 40° C., followed by two washes in 0.1×SSC, 0.1% SDS at 65° C. before exposure to X-AR film with intensifying screens at −70° C.

HindIII digested genomic DNA from the parental B cell line Raji showed three positive bands after hybridization with a full length CIITA cDNA probe, as well as a high background signal due to the Alu-repeat sequence described in the 3' untranslated region of the CIITA cDNA (see above). Hybridization was therefore performed with distinct fragments of the CIITA cDNA. As shown in FIG. 4B, the 1.8 kb central HindIII fragment of CIITA cDNA hybridizes to a 3.8 kb HindIII fragment in genomic DNA of the parental B cell line Raji. This band is completely absent in DNA from the mutant cell line RJ2.25 (FIG. 4B, probe b), even after prolonged exposure of the blots, indicating deletion of that central region of the CIITA gene on both chromosomes. The genomic HindIII fragments that hybridize respectively to a 5' and a 3' CIITA cDNA probe are both present, unaltered in length, in DNA from the mutant cell line (FIG. 4B, probes a and c). These two bands, however, display only half the signal intensity in RJ2.25 compared to wild type Raji DNA, suggesting the presence of only one copy of each of these two fragments in the mutant cell.

Finally, the analysis of CIITA mRNA by RNase protection showed, as expected from the complete deletion documented by Southern blots, an absence of signal with a probe located within the deleted central part of the CIITA cDNA (FIG. 5A). Interestingly, a probe corresponding to the 3' end of CIITA mRNA was protected (FIG. 5B), suggesting readthrough across the internal deletion observed in the mutated gene. These experiments offer direct evidence for the absence of an intact CIITA gene in regulatory mutant RJ2.25 and indicate that the irradiation used for the generation of the mutant line had lead to the complete loss of one CIITA allele, while inducing an internal deletion in the other.

EXAMPLE 5

Other HLA class II regulatory mutants are also corrected by CIITA

HLA class II negative regulatory mutant B lymphoblastoid cell lines have been generated independently of RJ2.25, and by different procedures, including different protocols of mutagenesis. The inventor tested two additional such cell lines to explore whether, like in RJ2.25 (FIG. 6, panel 2), CIITA cDNA could correct for HLA-DR expression. Mutant RM3 [Calman et al., J. Immunol. 139 (1987), 2489–2495] was produced by chemical mutagenesis and shown to correspond, like RJ2.25, to a recessive defect in HLA class II regulation. When class II negative RM3 mutant B cells were transfected with CIITA cDNA, normal expression of HLA-DR was restored, as shown in FIG. 6, panel 3. As in the case of the RJ2.25 mutant, HLA-DQ and —DP expression were restored as well (data not shown). The inventor also generated HLA class II-negative mutants from the same Raji parental B cell line, following mutagenesis with EMS. One such mutant (REM-34) was transfected with CIITA cDNA and analyzed for HLA-DR expression. As in the two previous cases, CIITA had restored expression of HLA class II molecules (FIG. 6, panel 4).

Differential expression of CIITA

MHC class II genes are only expressed in a limited number of cell types. To date however, the factors suspected of being involved in the control of MHC class II expression have not exhibited a pattern of expression that correlates with that of MHC class II genes [Glimcher et al., loc. cit.]. In order to address this question for CIITA, RNAse protection experiments were performed with several MHC class II negative and positive cell lines (FIG. 5c).

Two CIITA cDNA fragments were prepared as RNAse protection probes. The internal probe covers nucleotides 2049 (SfiI) to 1824 (NcoI) protecting 225 bp of CIITA mRNA. The 3' end probe is complementary to a 180 bp fragment spanning nucleotides 4520 to 4340 (HinfI) of CIITA. As a control a fragment was prepared which protects a 275 bp fragment of (bp 1228 to 953) of the TBP mRNA. From the linearized constructs $^{32}$P-UTP labeled riboprobes were generated by in-vitro transcription leaving 44, 44, and 60 bp non-complementary vector encoded overhangs. Hybridizatio of 10 ug of total RNA completed to 50 ug with yeast RNA was carried out in 80% formamide with 500,000 cpm of probe over night at 50° C.

After digestion with RNAses A and T1 [Sambrook et al., loc. cit.], the protected fragments were resolved by electrophoresis on 6% polyacrylamide, 8 M urea gels and visualized by autoradiography. Several EBV transformed B cell lines, as well as the class II positive colon carcinoma cell line CO115, showed expression of CIITA mRNA. In contrast, three HLA class II negative cell lines, 2102Ep, Andrews MOLT-4 and SK-N-AS, showed no signal for CIITA mRNA expression (FIG. 5C). From this initial study, the inventor concluded that CIITA expression is not ubiquitous but is itself regulated, with a pattern that seems to correlate with MHC class II expression.

EXAMPLE 6

CIITA cDNA can restore the expression of MHC class II molecules in cells from patients with hereditary MHC class II deficiency Hereditary MHC class II deficiency is a form of primary immunodeficiency with a total lack of expression of MHC class II genes. Patients suffering from this disease frequently die from multiple infections. The CIITA gene was found to correct the genetic defect in some of these patients (see FIG. 7). B lymphocytes from patients with MHC class II deficiency can be transfected with the CIITA cDNA in an appropriate vector which results in the re-expression of all MHC class II genes. This correction of a genetic defect in live cells by a cloned gene opens the way to gene therapy for this disease.

EXAMPLE 7

CIITA cDNA can induce the expression of MHC class molecules in different types of MHC class II negative cells Most of the cells of the body are normally MHC class II negative. In a number of situations, such as vaccination or induction of an immune response against cancer cells, it is desirable to induce or boost the expression of MHC class II genes in cells that are normally class II negative, in order to render these cells more immunogenic. The data illustrated in FIG. 8 show that this can indeed be achieved. Three different MHC class II negative human cell lines were transfected with CIITA cDNA, which was sufficient to induce expression of high levels of MHC class II surface molecules. This effect of CIITA cDNA has obvious implications for new strategies for vaccination and for gene therapy in cancer.

EXAMPLE 8

MHC class II molecules induced by the transactivator gene CIITA are highly efficient in peptide binding and in peptide-specific T lymphocyte activation Cells in which the expression of MHC class II molecules had been induced by the transactivator gene CIITA (as CIITA cDNA) were tested for their ability to bind exogenously provided peptides and to present such peptides to T cell clones. These CIITA transfectants were compared with the same cells where MHC class II expression had been induced by interferon gamma. The two types of cells expressed MHC class II molecules at the surface at a similar level. This experiment was done with T cell clones of the appropriate HLA-DR specificity and exhibiting specificity for the particular tetanus toxoid peptides used. Peptide-specific T cell activation by these two types of MHC class II positive cells was measured by $H^3$-thymidine incorporation, expressed as a stimulation index. In this particular experiment, melanoma cells were used as antigen-presenting cells.

As can be seen in FIG. 9, MHC class II negative, untransfected control cells failed to activate T lymphocytes.

Interferon gamma stimulated, MHC class II positive cells also failed to induce significant T cell activation, even at high peptide concentration. On the other hand, cells transfected with CIITA cDNA behave as highly efficiently antigen presenting cells and peptide-specific T cell activators. In agreement with these functional results, the peptide binding ability of these two types of MHC class II positive cells was drastically different, being low in the interferon activated cells and high in the CIITA transfectants. Thus, CIITA induces the expression of MHC class II molecules that are unusual in their highly efficient capacity to bind and to present peptides to T lymphocytes, leading to activation of these lymphocytes. CIITA can therefore be used to generate cells that exhibit a very high peptide-specific immunogenicity.

I claim:

1. A method for identifying a molecule as an inhibitor which suppresses the activity of a protein displaying CIITA activity, said activity being essential for the general control of MHC class II gene expression in vertebrate cells, comprising the steps of:

(a) contacting a group of molecules in vitro with a protein and screening for molecules which bind said protein, said protein being encoded by a DNA selected from the group consisting of:

(i) the DNA sequence shown in FIG. 3 (SEQ ID NO: 5);

(ii) a DNA sequence which encodes the amino acid sequence shown in FIG. 3 (SEQ ID NO:6);

(iii) DNA sequences which are hybridize to the DNA sequence that is complementary to the DNA sequence of (i), said hybridization being performed at 10° C. below the $T_m$ for one hour in Stratagene QuikHyb solution followed by two fifteen minute washes at room temperature with a 2X SSC buffer and 0.1% (w/v) SDS wash solution and two 15 minute washes in 0.1X SSC and 0.1% SDS at 65° C;

(iv) allelic variants or fragments of the DNA sequence of (i), (ii) or (iii); and (v) DNA sequences which are degenerate as a result of the genetic code to the DNA sequences of (iii) or (iv); and (b) identifying a molecule as an inhibitor which suppresses the activity of a protein displaying CIITA activity by contacting any one of those molecules which bind to said protein in step (a) with a protein displaying CIITA activity in a cell based assay and assaying for CIITA inhibition, wherein said CIITA activity results in the expression of HLA class II genes and wherein said inhibition is measured in said cell based assay by inhibition of HLA class II gene expression.

2. The method according to claim 1, wherein said CIITA protein has the amino acid sequence as shown in FIG. 3 (SEQ ID NO.: 6).

3. The method according to claim 1, wherein the cells used in said cell based assay are from CIITA negative cell lines stably transfected with CIITA cDNA under the control of a constitutive promoter.

4. The method according to claim 1, wherein said molecule is selected from the group consisting of:

(a) a synthetic organic chemical;

(b) a natural fermentation product;

(c) a substance extracted from a microorganism, plant or animal; and (d) a peptide.

* * * * *

UNITED STATES PATENT AND TRADEMARK OFFICE
CERTIFICATE OF CORRECTION

Page 1 of 2

PATENT NO. : 5,994,082
DATED : November 30, 1999
INVENTOR(S) : Bernard Mach

It is certified that error appears in the above-identified patent and that said Letters Patent is hereby Title page,
Item [56], last line of "Other Publications" change "Hereditiry" to --Hereditary--.
Column 1, line 58 change "have" to --has--.
Column 1, line 62 change "et al," to --et al.,--.
Column 2, line 31 new paragraph with "CIITA is".
Column 2, line 6 change "re-activation" to --reactivation--.
Column 2, line 50 change "is" to --it--.
Column 3, line 4 change "II-negative" to --II negative--.
Column 3, line 31 change "hybridise" to --hybridize--.
Column 4, line 29 change "an" to --a--.
Column 4, line 59 change "II-negative" to --II negative--.
Column 5, line 19 insert --,-- after "methods".
Column 5, line 24 change "inhibitors" to --inhibitor--.
Column 6, line 17 change "insulin" to --insulin--.
Column 6, line 57 change "cD4" to --CD4--.
Column 7, line 16 change "Tü22;" to --(Tü22;--.
Column 7, line 24 change "stop-codon" to --stop codon--.
Column 7, line 50 change "[Keo" to --[Kao--.
Column 7, line 51 change "CIITA specific" to --CIITA-specific--.
Column 8, line 16 no new paragraph with "B" (flush left).
Column 8, line 27 change "140B." to --143B.--.

UNITED STATES PATENT AND TRADEMARK OFFICE
CERTIFICATE OF CORRECTION

PATENT NO. : 5,994,082
DATED : November 30, 1999
INVENTOR(S) : Bernard Mach

It is certified that error appears in the above-identified patent and that said Letters Patent is hereby corrected as shown below:

```
Column  8, line 33 change "µug/ml" to --µg/ml--.
Column  8, line 67 delete "," after "Pst-EcoRV".
Column  9, line 19 change "sits" to --sites--.
Column 10, line 14 change "IN" to --In--.
Column 10, line 22 change "FACS can" to --FACScan--.
Column 10, line 33 change "AB-serum" to --AB serum--.
Column 11, line 31 change "re-transfected" to --retransfected--.
Column 12, line 49 change "³²p" to --³²P--.
Column 12, line 50 change "hygridisation" to --hybridization--.
Column 13, line  8 change "RNase" to --RNAse--.
Column 13, line 38 change "II-negative" to --II negative--.
Column 13, line 63 change "Hybridizatio" to --Hybridization--.
Column 27, line 29 delete "are".
Column 28, line 19 change "cell based" to --cell-based--.
Column 28, line 22 change "cell based" to --cell-based--.
Column 28, line 29 change "cell based" to --cell-based--.
```

Signed and Sealed this

Fifth Day of December, 2000

*Attest:*

Q. TODD DICKINSON

*Attesting Officer*     *Director of Patents and Trademarks*

```
                            SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
            (A) LENGTH: 19 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 1:

GAGCTCGGCC TCACTGGCC                                                   19

(2) INFORMATION FOR SEQ ID NO: 2:

(i) SEQUENCE CHARACTERISTICS:
            (A) LENGTH: 19 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 2:

GGCCAGTGAG GCCGGTACC                                                   19

(2) INFORMATION FOR SEQ ID NO: 3:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 3:

TGGCCGTCGA CTAC                                                        14

(2) INFORMATION FOR SEQ ID NO: 4:

(i) SEQUENCE CHARACTERISTICS:
            (A) LENGTH: 17 base pairs
```

```
            (B) TYPE: nucleic acid
            (C) STRANDEDNESS: single
            (D) TOPOLOGY: linear (ii) MOLECULE TYPE: cDNA (iii) HYPOTHETICAL: NO (iii) ANTI-SENSE: NO (xi) SEQUENCE DESCRIPTION: SEQ ID NO: 4:

GTAGTCGACG GCCAGTG                                                        17

(2) INFORMATION FOR SEQ ID NO: 5:

(i) SEQUENCE CHARACTERISTICS:
            (A) LENGTH: 4543 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 5:

TGATGAGGCT GTGTGCTTCT GAGCTGGGCA TCCGAAGGCA TCCTTGGGGA AGCTGAGGGC    60

ACGAGGAGGG GCTGCCAGAC TCCGGGAGCT GCTGCCTGGC TGGGATTCCT ACACAATGCG   120

TTGCCTGGCT CCACGCCCTG CTGGGTCCTA CCTGTCAGAG CCCCAAGGCA GCTCACAGTG   180

TGCCACCATG GAGTTGGGGC CCCTAGAAGG TGGCTACCTG GAGCTTCTTA ACAGCGATGC   240

TGACCCCCTG TGCCTCTACC ACTTCTATGA CCAGATGGAC CTGGCTGGAG AAGAAGAGAT   300

TGAGCTCTAC TCAGAACCCG ACACAGACAC CATCAACTGC GACCAGTTCA GCAGGCTGTT   360

GTGTGACATG GAAGGTGATG AAGAGACCAG GGAGGCTTAT GCCAATATCG CGGAACTGGA   420

CCAGTATGTC TTCCAGGACT CCCAGCTGGA GGGCCTGAGC AAGGACATTT TCAAGCACAT   480

AGGACCAGAT GAAGTGATCG GTGAGAGTAT GGAGATGCCA GCAGAAGTTG GGCAGAAAAG   540

TCAGAAAAGA CCCTTCCCAG AGGAGCTTCC GGCAGACCTG AAGCACTGGA AGCCAGCTGA   600

GCCCCCCACT GTGGTGACTG GCAGTCTCCT AGTGGGACCA GTGAGCGACT GCTCCACCCT   660

GCCCTGCCTG CCACTGCCTG CGCTGTTCAA CCAGGAGCCA GCCTCCGGCC AGATGCGCCT   720

GGAGAAAACC GACCAGATTC CCATGCCTTT CTCCAGTTCC TCGTTGAGCT GCCTGAATCT   780

CCCTGAGGGA CCCATCCAGT TTGTCCCCAC CATCTCCACT CTGCCCCATG GGCTCTGGCA   840

AATCTCTGAG GCTGGAACAG GGGTCTCCAG TATATTCATC TACCATGGTG AGGTGCCCCA   900

GGCCAGCCAA GTACCCCCTC CCAGTGGATT CACTGTCCAC GGCCTCCCAA CATCTCCAGA   960

CCGGCCAGGC TCCACCAGCC CCTTCGCTCC ATCAGCCACT GACCTGCCCA GCATGCCTGA  1020

ACCTGCCCTG ACCTCCCGAG CAAACATGAC AGAGCACAAG ACGTCCCCCA CCCAATGCCC  1080

GGCAGCTGGA GAGGTCTCCA ACAAGCTTCC AAAATGGCCT GAGCCGGTGG AGCAGTTCTA  1140

CCGCTCACTG CAGGACACGT ATGGTGCCGA GCCCGCAGGC CCGGATGGCA TCCTAGTGGA  1200

GGTGGATCTG GTGCAGGCCA GGCTGGAGAG GAGCAGCAGC AAGAGCCTGG AGCGGGAACT  1260

GGCCACCCCG GACTGGGCAG AACGGCAGCT GGCCCAAGGA GGCCTGGCTG AGGTGCTGTT  1320

GGCTGCCAAG GAGCACCGGC GGCCGCGTGA GACACGAGTG ATTGCTGTGC TGGGCAAAGC  1380

TGGTCAGGGC AAGAGCTATT GGGCTGGGGC AGTGAGCCGG GCCTGGGCTT GTGGCCGGCT  1440

TCCCCAGTAC GACTTTGTCT CTCTCTGTCC CTGCCATTGC TTGAACCGTC CGGGGGATGC  1500
```

```
CTATGGCCTG CAGGATCTGC TCTTCTCCCT GGGCCCACAG CCACTCGTGG CGGCCGATGA    1560

GGTTTTCAGC CACATCTTGA AGAGACCTGA CCGCGTTCTG CTCATCCTAG ACGCCTTCGA    1620

GGAGCTGGAA GCGCAAGATG GCTTCCTGCA CAGCACGTGC GGACCGGCAC CGGCGGAGCC    1680

CTGCTCCCTC CGGGGCTGC TGGCCGGCCT TTTCCAGAAG AAGCTGCTCC GAGGTTGCAC    1740

CCTCCTCCTC ACAGCCCGGC CCCGGGGCCG CCTGGTCCAG AGCCTGAGCA AGGCCGACGC    1800

CCTATTTGAG CTGTCCGGCT TCTCCATGGA GCAGGCCCAG GCATACGTGA TGCGCTACTT    1860

TGAGAGCTCA GGGATGACAG AGCACCAAGA CAGAGCCCTG ACGCTCCTCC GGGACCGGCC    1920

ACTTCTTCTC AGTCACAGCC ACAGCCCTAC TTTGTGCCGG GCAGTGTGCC AGCTCTCAGA    1980

GGCCCTGCTG GAGCTTGGGG AGGACGCCAA GCTGCCCTCC ACGCTCACGG GACTCTATGT    2040

CGGCCTGCTG GGCCGTGCAG CCCTCGACAG CCCCCCCGGG GCCCTGGCAG AGCTGGCCAA    2100

GCTGGCCTGG GAGCTGGGCC GCAGACATCA AAGTACCCTA CAGGAGGACC AGTTCCCATC    2160

CGCAGACGTG AGGACCTGGG CGATGGCCAA AGGCTTAGTC CAACACCCAC CGCGGGCCGC    2220

AGAGTCCGAG CTGGCCTTCC CCAGCTTCCT CCTGCAATGC TTCCTGGGGG CCCTGTGGCT    2280

GGCTCTGAGT GGCGAAATCA AGGACAAGGA GCTCCCGCAG TACCTAGCAT TGACCCCAAG    2340

GAAGAAGAGG CCCTATGACA ACTGGCTGGA GGGCGTGCCA CGCTTTCTGG CTGGGCTGAT    2400

CTTCCAGCCT CCCGCCCGCT GCCTGGGAGC CCTACTCGGG CCATCGGCGG CTGCCTCGGT    2460

GGACAGGAAG CAGAAGGTGC TTGCGAGGTA CCTGAAGCGG CTGCAGCCGG GACACTGCG    2520

GGCGCGGCAG CTGCTTGAGC TGCTGCACTG CGCCCACGAG GCCGAGGAGG CTGGAATTTG    2580

GCAGCACGTG GTACAGGAGC TCCCCGGCCG CCTCTCTTTT CTGGGCACCC GCCTCACGCC    2640

TCCTGATGCA CATGTACTGG GCAAGGCCTT GGAGGCGGCG GGCCAAGACT TCTCCCTGGA    2700

CCTCCGCAGC ACTGGCATTT GCCCCTCTGG ATTGGGGAGC CTCGTGGGAC TCAGCTGTGT    2760

CACCCGTTTC AGGGCTGCCT TGAGCGACAC GGTGGCGCTG TGGGAGTCCC TGCGGCAGCA    2820

TGGGGAGACC AAGCTACTTC AGGCAGCAGA GGAGAAGTTC ACCATCGAGC CTTTCAAAGC    2880

CAAGTCCCTG AAGGATGTGG AAGACCTGGG AAAGCTTGTG CAGACTCAGA GGACGAGAAG    2940

TTCCTCGGAA GACACAGCTG GGGAGCTCCC TGCTGTTCGG GACCTAAAGA AACTGGAGTT    3000

TGCGCTGGGC CCTGTCTCAG GCCCCCAGGC TTTCCCCAAA CTGGTGCGGA TCCTCACGGC    3060

CTTTTCCTCC CTGCAGCATC TGGACCTGGA TGCGCTGAGT GAGAACAAGA TCGGGGACGA    3120

GGGTGTCTCG CAGCTCTCAG CCACCTTCCC CCAGCTGAAG TCCTTGGAAA CCCTCAATCT    3180

GTCCCAGAAC AACATCACTG ACCTGGGTGC CTACAAACTC GCCGAGGCCC TGCCTTCGCT    3240

CGCTGCATCC CTGCTCAGGC TAAGCTTGTA CAATAACTGC ATCTGCGACG TGGGAGCCGA    3300

GAGCTTGGCT CGTGTGCTTC CGGACATGGT GTCCCTCCGG GTGATGGACG TCCAGTACAA    3360

CAAGTTCACG GCTGCCGGGG CCCAGCAGCT CGCTGCCAGC CTTCGGAGGT GTCCTCATGT    3420

GGAGACGCTG GCGATGTGGA CGCCCACCAT CCCATTCAGT GTCCAGGAAC ACCTGCAACA    3480

ACAGGATTCA CGGATCAGCC TGAGATGATC CCAGCTGTGC TCTGGACAGG CATGTTCTCT    3540

GAGGACACTA ACCACGCTGG ACCTTGAACT GGGTACTTGT GGACACAGCT CTTCTCCAGG    3600

CTGTATCCCA TGAGGCCTCA GCATCCTGGC ACCCGGCCCC TGCTGGTTCA GGGTTGGCCC    3660

CTGCCCGGCT GCGGAATGAA CCACATCTTG CTCTGCTGAC AGACACAGGC CCGGCTCCAG    3720

GCTCCTTTAG CGCCCAGTTG GGTGGATGCC TGGTGGCAGC TGCGGTCCAC CCAGGAGCCC    3780

CGAGGCCTTC TCTGAAGGAC ATTGCGGACA GCCACGGCCA GGCCAGAGGG AGTGACAGAG    3840

GCAGCCCCAT TCTGCCTGCC CAGGCCCCTG CCACCCTGGG GAGAAAGTAC TTCTTTTTTT    3900
```

```
TTATTTTTAG ACAGAGTCTC ACTGTTGCCC AGGCTGGCGT GCAGTGGTGC GATCTGGGTT    3960

CACTGCAACC TCCGCCTCTT GGGTTCAAGC GATTCTTCTG CTTCAGCCTC CCGAGTAGCT    4020

GGGACTACAG GCACCCACCA TCATGTCTGG CTAATTTTTC ATTTTTAGTA GAGACAGGGT    4080

TTTGCCATGT TGGCCAGGCT GGTCTCAAAC TCTTGACCTC AGGTGATCCA CCCACCTCAG    4140

CCTCCCAAAG TGCTGGGGAT TACAAGCGTG AGCCACTGCA CCGGGCCACA GAGAAAGTAC    4200

TTCTCCACCC TGCTCTCCGA CCAGACACCT TGACAGGGCA CACCGGGCAC TCAGAAGACA    4260

CTGATGGGCA ACCCCCAGCC TGCTAATTCC CCAGATTGCA ACAGGCTGGG CTTCAGTGGC    4320

AGGCTGCTTT TGTCTATGGG ACTCAATGCA CTGACATTGT TGGCCAAAGC CAAAGCTAGG    4380

CCTGGCCAGA TGCACCAGGC CCTTAGCAGG GAAACAGCTA ATGGGACACT AATGGGGCGG    4440

TGAGAGGGGA ACAGACTGGA AGCACAGCTT CATTTCCTGT GTCTTTTTTC ACTACATTAT    4500

AAATGTCTCT TTAATGTCAC AAAAAAAAAA AAAAAAAAAA AAA                      4543
```

(2) INFORMATION FOR SEQ ID NO: 6:

(i) SEQUENCE CHARACTERISTICS:
        (A) LENGTH: 1130 amino acids
        (B) TYPE: amino acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 6:

```
Met Arg Cys Leu Ala Pro Arg Pro Ala Gly Ser Tyr Leu Ser Glu Pro
1               5                  10                  15

Gln Gly Ser Ser Gln Cys Ala Thr Met Glu Leu Gly Pro Leu Glu Gly
            20                  25                  30

Gly Tyr Leu Glu Leu Leu Asn Ser Asp Ala Asp Pro Leu Cys Leu Tyr
        35                  40                  45

His Phe Tyr Asp Gln Met Asp Leu Ala Gly Glu Glu Ile Glu Leu
    50                  55                  60

Tyr Ser Glu Pro Asp Thr Asp Thr Ile Asn Cys Asp Gln Phe Ser Arg
65                  70                  75                  80

Leu Leu Cys Asp Met Glu Gly Asp Glu Glu Thr Arg Glu Ala Tyr Ala
                85                  90                  95

Asn Ile Ala Glu Leu Asp Gln Tyr Val Phe Gln Asp Ser Gln Leu Glu
            100                 105                 110

Gly Leu Ser Lys Asp Ile Phe Lys His Ile Gly Pro Asp Glu Val Ile
        115                 120                 125

Gly Glu Ser Met Glu Met Pro Ala Glu Val Gly Gln Lys Ser Gln Lys
    130                 135                 140

Arg Pro Phe Pro Glu Glu Leu Pro Ala Asp Leu Lys His Trp Lys Pro
145                 150                 155                 160

Ala Glu Pro Pro Thr Val Val Thr Gly Ser Leu Leu Val Gly Pro Val
                165                 170                 175

Ser Asp Cys Ser Thr Leu Pro Cys Leu Pro Leu Pro Ala Leu Phe Asn
            180                 185                 190

Gln Glu Pro Ala Ser Gly Gln Met Arg Leu Glu Lys Thr Asp Gln Ile
        195                 200                 205

Pro Met Pro Phe Ser Ser Ser Ser Leu Ser Cys Leu Asn Leu Pro Glu
```

-continued

```
            210                 215                 220
Gly Pro Ile Gln Phe Val Pro Thr Ile Ser Thr Leu Pro His Gly Leu
225                 230                 235                 240

Trp Gln Ile Ser Glu Ala Gly Thr Gly Val Ser Ser Ile Phe Ile Tyr
                245                 250                 255

His Gly Glu Val Pro Gln Ala Ser Gln Val Pro Pro Ser Gly Phe
            260                 265                 270

Thr Val His Gly Leu Pro Thr Ser Pro Asp Arg Pro Gly Ser Thr Ser
            275                 280                 285

Pro Phe Ala Pro Ser Ala Thr Asp Leu Pro Ser Met Pro Glu Pro Ala
290                 295                 300

Leu Thr Ser Arg Ala Asn Met Thr Glu His Lys Thr Ser Pro Thr Gln
305                 310                 315                 320

Cys Pro Ala Ala Gly Glu Val Ser Asn Lys Leu Pro Lys Trp Pro Glu
                325                 330                 335

Pro Val Glu Gln Phe Tyr Arg Ser Leu Gln Asp Thr Tyr Gly Ala Glu
                340                 345                 350

Pro Ala Gly Pro Asp Gly Ile Leu Val Glu Val Asp Leu Val Gln Ala
            355                 360                 365

Arg Leu Glu Arg Ser Ser Lys Ser Leu Glu Arg Glu Leu Ala Thr
            370                 375                 380

Pro Asp Trp Ala Glu Arg Gln Leu Ala Gln Gly Gly Leu Ala Glu Val
385                 390                 395                 400

Leu Leu Ala Ala Lys Glu His Arg Arg Pro Arg Glu Thr Arg Val Ile
                405                 410                 415

Ala Val Leu Gly Lys Ala Gly Gln Gly Lys Ser Tyr Trp Ala Gly Ala
                420                 425                 430

Val Ser Arg Ala Trp Ala Cys Gly Arg Leu Pro Gln Tyr Asp Phe Val
            435                 440                 445

Phe Ser Val Pro Cys His Cys Leu Asn Arg Pro Gly Asp Ala Tyr Gly
450                 455                 460

Leu Gln Asp Leu Leu Phe Ser Leu Gly Pro Gln Pro Leu Val Ala Ala
465                 470                 475                 480

Asp Glu Val Phe Ser His Ile Leu Lys Arg Pro Asp Arg Val Leu Leu
                485                 490                 495

Ile Leu Asp Ala Phe Glu Glu Leu Glu Ala Gln Asp Gly Phe Leu His
                500                 505                 510

Ser Thr Cys Gly Pro Ala Pro Ala Glu Pro Cys Ser Leu Arg Gly Leu
            515                 520                 525

Leu Ala Gly Leu Phe Gln Lys Lys Leu Leu Arg Gly Cys Thr Leu Leu
530                 535                 540

Leu Thr Ala Arg Pro Arg Gly Arg Leu Val Gln Ser Leu Ser Lys Ala
545                 550                 555                 560

Asp Ala Leu Phe Glu Leu Ser Gly Phe Ser Met Glu Gln Ala Gln Ala
                565                 570                 575

Tyr Val Met Arg Tyr Phe Glu Ser Ser Gly Met Thr Glu His Gln Asp
                580                 585                 590

Arg Ala Leu Thr Leu Leu Arg Asp Arg Pro Leu Leu Leu Ser His Ser
            595                 600                 605

His Ser Pro Thr Leu Cys Arg Ala Val Cys Gln Leu Ser Glu Ala Leu
            610                 615                 620

Leu Glu Leu Gly Glu Asp Ala Lys Leu Pro Ser Thr Leu Thr Gly Leu
625                 630                 635                 640
```

-continued

```
Tyr Val Gly Leu Leu Gly Arg Ala Ala Leu Asp Ser Pro Pro Gly Ala
                645                 650                 655
Leu Ala Glu Leu Ala Lys Leu Ala Trp Glu Leu Gly Arg Arg His Gln
            660                 665                 670
Ser Thr Leu Gln Glu Asp Gln Phe Pro Ser Ala Asp Val Arg Thr Trp
        675                 680                 685
Ala Met Ala Lys Gly Leu Val Gln His Pro Pro Arg Ala Ala Glu Ser
    690                 695                 700
Glu Leu Ala Phe Pro Ser Phe Leu Leu Gln Cys Phe Leu Gly Ala Leu
705                 710                 715                 720
Trp Leu Ala Leu Ser Gly Glu Ile Lys Asp Lys Leu Pro Gln Tyr
                725                 730                 735
Leu Ala Leu Thr Pro Arg Lys Lys Arg Pro Tyr Asp Asn Trp Leu Glu
            740                 745                 750
Gly Val Pro Arg Phe Leu Ala Gly Leu Ile Phe Gln Pro Pro Ala Arg
        755                 760                 765
Cys Leu Gly Ala Leu Leu Gly Pro Ser Ala Ala Ser Val Asp Arg
    770                 775                 780
Lys Gln Lys Val Leu Ala Arg Tyr Leu Lys Arg Leu Gln Pro Gly Thr
785                 790                 795                 800
Leu Arg Ala Arg Gln Leu Leu Glu Leu Leu His Cys Ala His Glu Ala
                805                 810                 815
Glu Glu Ala Gly Ile Trp Gln His Val Val Gln Glu Leu Pro Gly Arg
            820                 825                 830
Leu Ser Phe Leu Gly Thr Arg Leu Thr Pro Pro Asp Ala His Val Leu
        835                 840                 845
Gly Lys Ala Leu Glu Ala Ala Gly Gln Asp Phe Ser Leu Asp Leu Arg
    850                 855                 860
Ser Thr Gly Ile Cys Pro Ser Gly Leu Gly Ser Leu Val Gly Leu Ser
865                 870                 875                 880
Cys Val Thr Arg Phe Arg Ala Ala Leu Ser Asp Thr Val Ala Leu Trp
                885                 890                 895
Glu Ser Leu Arg Gln His Gly Glu Thr Lys Leu Leu Gln Ala Ala Glu
            900                 905                 910
Glu Lys Phe Thr Ile Glu Pro Phe Lys Ala Lys Ser Leu Lys Asp Val
        915                 920                 925
Glu Asp Leu Gly Lys Leu Val Gln Thr Gln Arg Thr Arg Ser Ser Ser
    930                 935                 940
Glu Asp Thr Ala Gly Glu Leu Pro Ala Val Arg Asp Leu Lys Lys Leu
945                 950                 955                 960
Glu Phe Ala Leu Gly Pro Val Ser Gly Pro Gln Ala Phe Pro Lys Leu
                965                 970                 975
Val Arg Ile Leu Thr Ala Phe Ser Ser Leu Gln His Leu Asp Leu Asp
            980                 985                 990
Ala Leu Ser Glu Asn Lys Ile Gly Asp Glu Gly Val Ser Gln Leu Ser
        995                 1000                1005
Ala Thr Phe Pro Gln Leu Lys Ser Leu Glu Thr Leu Asn Leu Ser Gln
    1010                1015                1020
Asn Asn Ile Thr Asp Leu Gly Ala Tyr Lys Leu Ala Glu Ala Leu Pro
1025                1030                1035                1040
Ser Leu Ala Ala Ser Leu Leu Arg Leu Ser Leu Tyr Asn Asn Cys Ile
                1045                1050                1055
Cys Asp Val Gly Ala Glu Ser Leu Ala Arg Val Leu Pro Asp Met Val
            1060                1065                1070
```

```
Ser Leu Arg Val Met Asp Val Gln Tyr Asn Lys Phe Thr Ala Ala Gly
        1075            1080            1085

Ala Gln Gln Leu Ala Ala Ser Leu Arg Arg Cys Pro His Val Glu Thr
        1090            1095            1100

Leu Ala Met Trp Thr Pro Thr Ile Pro Phe Ser Val Gln Glu His Leu
1105            1110            1115            1120

Gln Gln Gln Asp Ser Arg Ile Ser Leu Arg
            1125            1130
```